(12) United States Patent
Hopper et al.

(10) Patent No.: US 10,390,992 B2
(45) Date of Patent: Aug. 27, 2019

(54) THERMAL CONTROL SYSTEM

(71) Applicant: Stryker Corporation, Kalamazoo, MI (US)

(72) Inventors: Christopher John Hopper, Kalamazoo, MI (US); Brian Schultz, Pine Island, MN (US); Roy E Holmberg, III, Portage, MI (US); Jonathan David Campbell, Scotts, MI (US); Marco Constant, Fort Erie (CA)

(73) Assignee: Stryker Corporation, Kalamazoo, MI (US)

( * ) Notice: Subject to any disclaimer, the term of this patent is extended or adjusted under 35 U.S.C. 154(b) by 1022 days.

(21) Appl. No.: 14/282,383

(22) Filed: May 20, 2014

(65) Prior Publication Data

US 2014/0343639 A1 Nov. 20, 2014

Related U.S. Application Data

(60) Provisional application No. 61/825,225, filed on May 20, 2013.

(51) Int. Cl.
*A61F 7/00* (2006.01)
*A61B 18/00* (2006.01)

(52) U.S. Cl.
CPC .. *A61F 7/0085* (2013.01); *A61B 2018/00797* (2013.01); *A61B 2018/00863* (2013.01);
(Continued)

(58) Field of Classification Search
CPC .................................................. A61F 7/0085
See application file for complete search history.

(56) References Cited

U.S. PATENT DOCUMENTS 3,625,279 A  12/1971  Mayo et al.
3,872,726 A   3/1975  Kauffeld et al.
(Continued)

FOREIGN PATENT DOCUMENTS

EP    0448414 B1   10/1994
EP    2514453 A1   10/2012
(Continued)

OTHER PUBLICATIONS

PCT International Search Report and Written Opinion for PCT/US2014/038801, the international counterpart to U.S. Appl. No. 14/282,383.
(Continued)

*Primary Examiner* — Luther Behringer
(74) *Attorney, Agent, or Firm* — Warner Norcross + Judd LLP

(57) ABSTRACT

A thermal control unit for delivering temperature-controlled fluid to one or more patient therapy devices (e.g. pads, blankets, etc.) that are in contact with a patient is disclosed. The thermal control unit allows multiple patient therapy devices to be fluidly coupled thereto and to individually monitor the temperatures, flow rates, and/or connections/disconnections of the patient therapy devices. A user interface enables a user to designate outlet ports to the therapy devices as active or inactive, and the control unit provides notifications to the user if any of the active ports experience an undesired condition, or if a patient therapy device is connected to an inactive port. The user interface further allows the user to designate one of multiple patient temperature probes as a primary probe. The primary probe is used to control the temperature of the fluid circulating through the control unit.

18 Claims, 23 Drawing Sheets

(52) U.S. Cl.
CPC ......... *A61F 2007/0054* (2013.01); *A61F 2007/0086* (2013.01); *A61F 2007/0093* (2013.01); *A61F 2007/0096* (2013.01)

(56) References Cited

U.S. PATENT DOCUMENTS

| | | | |
|---|---|---|---|
| 3,894,213 | A | 7/1975 | Agarwala |
| 3,995,621 | A | 12/1976 | Fletcher et al. |
| 4,149,529 | A | 4/1979 | Copeland et al. |
| 4,459,468 | A | 7/1984 | Bailey |
| 4,547,977 | A | 10/1985 | Tenedini et al. |
| 4,569,674 | A * | 2/1986 | Phillips ............ A61M 27/00 604/119 |
| 4,680,445 | A | 7/1987 | Ogawa |
| 4,691,762 | A | 9/1987 | Elkins et al. |
| 4,707,587 | A | 11/1987 | Greenblatt |
| 4,844,072 | A | 7/1989 | French et al. |
| 5,197,537 | A | 3/1993 | Chigira et al. |
| 5,265,005 | A * | 11/1993 | Schmidt ............ G05B 19/052 700/18 |
| 5,381,954 | A | 1/1995 | Tokizaki |
| 5,486,207 | A | 1/1996 | Mahawili |
| 5,562,604 | A | 10/1996 | Yablon et al. |
| 5,634,940 | A | 6/1997 | Panyard |
| 5,711,155 | A | 1/1998 | De Vilbiss et al. |
| 5,759,162 | A | 6/1998 | Oppelt et al. |
| 5,862,675 | A | 1/1999 | Scaringe et al. |
| 5,865,841 | A | 2/1999 | Kolen et al. |
| 5,871,526 | A | 2/1999 | Gibbs et al. |
| 5,894,615 | A | 4/1999 | Alexander |
| 5,895,418 | A | 4/1999 | Saringer |
| 5,948,012 | A | 9/1999 | Mahaffey et al. |
| 5,980,561 | A | 11/1999 | Kolen et al. |
| 6,086,609 | A | 7/2000 | Buckley |
| 6,091,060 | A | 7/2000 | Getchel et al. |
| 6,188,930 | B1 | 2/2001 | Carson |
| 6,197,045 | B1 | 3/2001 | Carson |
| 6,231,594 | B1 | 5/2001 | Dae |
| 6,290,717 | B1 | 9/2001 | Philips |
| 6,338,727 | B1 | 1/2002 | Noda et al. |
| 6,350,276 | B1 | 2/2002 | Knowlton |
| 6,352,550 | B1 | 3/2002 | Gildersleeve et al. |
| 6,375,674 | B1 | 4/2002 | Carson |
| 6,461,379 | B1 | 10/2002 | Carson et al. |
| 6,551,348 | B1 | 4/2003 | Blalock et al. |
| 6,620,187 | B2 | 9/2003 | Carson et al. |
| 6,620,188 | B1 | 9/2003 | Ginsburg et al. |
| 6,645,232 | B2 | 11/2003 | Carson |
| 6,648,905 | B2 | 11/2003 | Hoglund et al. |
| 6,660,027 | B2 | 12/2003 | Gruszecki et al. |
| 6,669,715 | B2 | 12/2003 | Hoglund et al. |
| D487,147 | S | 2/2004 | Ellingboe et al. |
| 6,692,518 | B2 | 2/2004 | Carson |
| 6,695,874 | B2 | 2/2004 | Machold et al. |
| 6,699,267 | B2 | 3/2004 | Voorhees et al. |
| 6,749,624 | B2 | 6/2004 | Knowlton |
| D492,773 | S | 7/2004 | Ellingboe et al. |
| 6,764,391 | B1 | 7/2004 | Grant et al. |
| 6,799,063 | B2 | 9/2004 | Carson |
| 6,802,855 | B2 | 10/2004 | Ellingboe et al. |
| 6,818,012 | B2 | 11/2004 | Ellingboe |
| 6,827,728 | B2 | 12/2004 | Ellingboe et al. |
| 6,921,198 | B2 | 7/2005 | Gruszecki et al. |
| 6,969,399 | B2 | 11/2005 | Schock et al. |
| 7,056,334 | B2 | 6/2006 | Lennox |
| 7,160,259 | B2 | 1/2007 | Tardy et al. |
| 7,640,768 | B2 | 1/2010 | Noda et al. |
| 7,828,831 | B1 | 11/2010 | Tanhehco et al. |
| 8,097,030 | B2 | 1/2012 | Stelea et al. |
| 8,706,207 | B2 | 4/2014 | Flint |
| 2002/0026225 | A1 * | 2/2002 | Segal ............ A61N 1/326 607/89 |
| 2004/0165646 | A1 | 8/2004 | Shidemantle et al. |
| 2004/0210283 | A1 | 10/2004 | Rose et al. |
| 2006/0048520 | A1 | 3/2006 | Huang et al. |
| 2006/0235497 | A1 | 10/2006 | Zanotti |
| 2006/0287697 | A1 | 12/2006 | Lennox |
| 2007/0021808 | A1 | 1/2007 | Rojas |
| 2007/0162097 | A9 | 7/2007 | Rojas |
| 2008/0058697 | A1 | 3/2008 | Kamen et al. |
| 2009/0099629 | A1 | 4/2009 | Carson et al. |
| 2009/0240312 | A1 | 9/2009 | Koewler |
| 2010/0139294 | A1 | 6/2010 | Lowe et al. |
| 2011/0152982 | A1 | 6/2011 | Richardson |
| 2013/0245519 | A1 * | 9/2013 | Edelman ............ A61H 9/0078 601/152 |

FOREIGN PATENT DOCUMENTS

| | | |
|---|---|---|
| JP | 5023375 A | 2/1993 |
| WO | 200154635 A1 | 8/2001 |
| WO | 200238091 A1 | 5/2002 |
| WO | 2003030790 A1 | 4/2003 |
| WO | 2004006814 A2 | 1/2004 |
| WO | 2005117546 A2 | 12/2005 |

OTHER PUBLICATIONS

Gaymar—Service Manual—Medi-Therm III Hyper/Hypothermia Machine, Ref MTA7912, dated Nov. 2009.
European Search Report dated Nov. 29, 2016, for European patent application 14801032, corresponding to U.S. Appl. No. 14/282,383.

* cited by examiner

THERMAL CONTROL SYSTEM

CROSS-REFERENCE TO RELATED APPLICATIONS

This application claims priority to U.S. provisional patent application Ser. No. 61/825,225 filed May 20, 2013 by applicants Christopher Hopper et al. and entitled THERMAL CONTROL SYSTEM, the complete disclosure of which is hereby incorporated herein by reference.

BACKGROUND OF THE INVENTION

The present invention relates to a thermal control unit and system for controlling the temperature of circulating fluid which is delivered to one or more thermal pads positioned in contact with a patient.

Thermal control systems are known in the art for controlling the temperature of a patient by supplying temperature-controlled fluid to one or more pads, blankets, or similar structures, that are positioned in contact with, or adjacent to, a patient. The temperature of the fluid is controlled by a thermal unit that provides fluid to the pads or blankets. After passing through the pads or blankets, the fluid is returned to the control unit where any necessary adjustments to the returning fluid temperature are made before being pumped back to the pad or blanket. In some instances, the temperature of the fluid is controlled to a target temperature, while in other instances the temperature of the fluid is controlled in order to effectuate a change or steady-state patient temperature. When controlling a patient's temperature, a patient temperature probe may be attached to the control unit in order to provide patient temperature readings as feedback to the control unit so that it can make the necessary temperature adjustments.

SUMMARY OF THE INVENTION

The present invention provides various improved aspects to a thermal control system. In one embodiment, the present invention includes a thermal control unit that takes less time to bring the regulated fluid to the desired temperature. In other embodiments, a thermal control unit is provided that is tank-less such that substantially all of the fluid whose temperature is being controlled is in circulation. In still other embodiments, a thermal control unit is provided with a removable reservoir that improves the convenience of using the unit, and/or a large touch screen control panel with a smaller LCD screen that provides an intuitive graphical user interface for controlling the system. In yet other embodiments, still other features and/or advantages are provided.

According to one embodiment, a thermal control unit is provided that is adapted to deliver temperature controlled fluid to a patient. The thermal control unit includes a plurality of outlets adapted to fluidly connect to a plurality of patient therapy devices, such as, but not limited to, one or more thermal pads, blankets, vests, boots, socks, caps, or the like. The outlets are adapted to deliver the temperature controlled fluid to the patient therapy devices when the patient therapy devices are connected thereto. The thermal control unit includes a sensing subsystem to monitor the connection status of the outlets and/or the utilization of the fluid circuit(s) defined between the control unit and the patient therapy device(s). The thermal control unit further includes an indicator adapted to provide an indication to a user if a patient therapy device is added to, or removed from, any one or more of the outlets while the control unit is delivering the temperature controlled fluid to the patient.

According to another embodiment, a thermal control unit is provided that includes first and second fluid outlet, first and second fluid inlets, a heat exchanger, a pump, a sensing subsystem, and a controller. The first and second fluid outlets are adapted to be fluidly coupled to first and second fluid supply lines, respectively. The first and second fluid inlets are adapted to be fluidly coupled to first and second fluid return lines, respectively. The pump circulates fluid from the first and second fluid inlets through the heat exchanger and to the first and second fluid outlets. The sensing subsystem is adapted to detect if the first fluid outlet becomes connected to, disconnected from, or re-connected to the first fluid supply line, or if the flow status at the first fluid supply line changes. The sensing subsystem is also adapted to detect if the second fluid outlet becomes connected to, disconnected from, or re-connected to the second fluid supply line, or if the flow status at the second fluid supply line changes. The controller is in communication with the pump, the heat exchanger, and the sensing subsystem, and the controller is adapted to provide an indication to a user if the first fluid outlet becomes disconnected from the first fluid supply line, or the second fluid outlet become disconnected from the second fluid supply line.

In another embodiment, the sensing subsystem is adapted to differentiate between various types of supply lines and/or individual supply lines.

In another embodiment, a thermal control unit is provided that includes a heat exchanger, a pump, first and second flow meters, and a controller. The pump circulates fluid from first and second inlets through the heat exchanger to first and second outlets. The first and second outlets are adapted to supply temperature-controlled fluid to a patient therapy device, and the first and second inlets are adapted to receive the fluid back after passing through the patient therapy device. The first flow meter is adapted to measure a first flow rate of the fluid through either the first outlet or the first inlet. The second flow meter is adapted to measure a second flow rate of the fluid through either the second outlet or the second inlet. The controller is in electrical communication with the first and second flow meters and is adapted to generate a first alert if the first flow rate measured by the first flow meter is less than a first threshold, and to generate a second alert if the second flow rate measured by the second flow meter is less than a second threshold.

According to other aspects, the first and second thresholds may be the same. The control unit may include a user interface in electrical communication with the controller wherein the user interface includes a first indicator for indicating the first alert and a second indicator for indicating the second alert.

The thermal control unit may also include a third inlet and a third outlet in the manifold, and a third flow meter adapted to measure a third flow rate of the fluid through either the third outlet or the third inlet. When the third flow meter is included, the controller is adapted to generate a third alert if the third flow rate measured by the third flow meter is less than a third threshold.

The thermal control unit may include a graphical user interface in electrical communication with the controller, wherein the user interface includes a first graphic that is illuminated a first color when the first flow rate exceeds the first threshold and a second color when the first flow rate is less than the first threshold. The user interface may further include a second graphic that is illuminated the first color when the second flow rate exceeds the second threshold, and the second color when the second flow rate is less than the second threshold. In addition, the first graphic may be unilluminated when the first flow rate is zero, and the second graphic may be unilluminated when the second flow rate is zero. The first color may be green and the second color may be yellow.

A first temperature sensor may be included that is positioned to measure a first temperature of fluid returning to the first fluid inlet; and a second temperature sensor may be included that is positioned to measure a second temperature of fluid returning to the second fluid inlet. The controller is adapted to display the first and second temperatures on a user interface.

The controller may be adapted to operate in a plurality of modes that are selectable by a user, wherein in a first one of the plurality of modes the controller seeks to maintain a constant temperature in fluid delivered to the first and second outlets; and wherein in a second one of the plurality of modes the controller seeks to control a temperature of a patient.

The thermal control unit may also include a first patient temperature probe port and a second patient temperature probe port, wherein each of the first and second patient temperature probe ports are adapted to receive a patient temperature probe that measures a temperature of a patient. The controller may be adapted to control a temperature of fluid delivered to the first and second outlets based on temperature information received through either the first patient temperature probe port or the second patient temperature probe port. Further, the user interface may be adapted to allow a user to choose the first patient temperature probe port or the second patient temperature probe port, or both the first and second patient temperature probe ports, for use by the controller in controlling the temperature of fluid delivered to the first and second outlets.

The thermal control unit may include a removable reservoir adapted to be lifted out of the control unit. A reservoir sensor can be included with the thermal control unit that detects the absence or presence of the removable reservoir, wherein the reservoir sensor electrically communicates with the controller. The controller issues an alert if the reservoir sensor detects the absence of the removable reservoir. A valve may be integrated into a bottom wall of the removable reservoir wherein the valve is adapted to automatically open when the removable reservoir is inserted into the control unit. When the removable reservoir is attached to the thermal control unit, any fluid that remains within the removable reservoir is substantially thermally isolated from fluid flowing through the heat exchanger of the thermal control unit, thereby avoiding adding to the specific heat load of the thermal control unit, which speeds up the ability of the thermal control unit to change the temperature of the circulating fluid.

The thermal control unit may also include a drain for draining fluid from the thermal control unit wherein the drain is positioned on the control unit such that the removable reservoir automatically shuts the drain when the removable reservoir is coupled to the thermal control unit, thereby preventing the accidental drainage of the reservoir fluid into the thermal control unit and out of the drain of the thermal control unit.

According to another embodiment, a thermal control unit is provided that includes a heat exchanger, a pump, a first flow meter, a second flow meter, a user interface, and a controller. The pump circulates fluid from first and second inlets through the heat exchanger to first and second outlets. The first and second outlets are adapted to supply temperature-controlled fluid to a patient therapy device, and the first and second inlets are adapted to receive the fluid back after passing through the patient therapy device. The first flow meter is adapted to measure a first flow rate of the fluid through either the first outlet or the first inlet, and the second flow meter is adapted to measure a second flow rate through either the second outlet or the second inlet. The controller is in electrical communication with the first and second flow meters and the user interface, and the controller is adapted to cause the user interface to prompt a caregiver for confirmation if the first flow meter or second flow meter detects a decrease in fluid flow to a rate below a threshold.

In some embodiments, the threshold may be on the order of a half of a liter per minute. The prompting of the caregiver for confirmation may query the user whether or not the user intended to decrease the fluid flow to a rate below the threshold. The user interface may be configured such that it continues to prompt the caregiver for confirmation until the user responds to the confirmation prompt.

According to yet another embodiment, a thermal control unit is provided that includes a heat exchanger, a pump, first and second patient temperature probe ports, a user interface, and a controller. The pump circulates fluid through the heat exchanger and between an outlet and an inlet on the control unit that are adapted, respectively, to supply temperature-controlled fluid to a patient therapy device and to receive the fluid back after passing through the patient therapy device. The user interface is adapted to allow a user to designate which of the first and second patient temperature probe ports is a primary port. The controller is in electrical communication with the first and second patient temperature probe ports, and the controller is adapted to control a temperature of the fluid in the thermal control unit based on temperature readings supplied through the one of the first and second patient temperature probe ports that has been designated by the user as the primary port.

In an alternative embodiment, the user interface is further adapted to allow a user to designate both the first and second patient temperature probe ports as primary ports, thereby causing the control unit to use the readings from both of the temperature probe ports in controlling the temperature of the circulating fluid.

In some embodiments, the controller—when controlling the temperature of the fluid in the thermal control unit—does not use temperature readings from the one of the first and second patient temperature probe ports that has not been designated by the user as the primary port.

According to still another embodiment, a thermal control unit is provided that includes a heat exchanger, a pump, a manifold, an air pressure sensor, a channel, and a controller. The pump circulates liquid through the heat exchanger, and the manifold is in liquid communication with the pump. The channel has first and second ends and the first end is in liquid communication with the manifold while the second end is in gaseous communication with the air pressure sensor. The controller is in electrical communication with the air pressure sensor and uses signals from the air pressure sensor to determine a level of liquid in the thermal control unit.

In some embodiments, the channel may be a tube. Whether the channel is a tube or not, it may also include a valve at its second end that is adapted to automatically and hermetically seal the second end when the second end is disconnected from the air pressure sensor.

In still other embodiments, the controller is adapted to oversee the temperature control and delivery of fluid to multiple supply lines that have different target fluid temperatures and/or different target flow rates. The target temperatures and flow rates may be user-designated or they may be automatically generated by the controller based upon patient temperature readings and one or more user-designated target patient temperatures.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and is capable of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

DETAILED DESCRIPTION OF THE EMBODIMENTS

Figure 1:
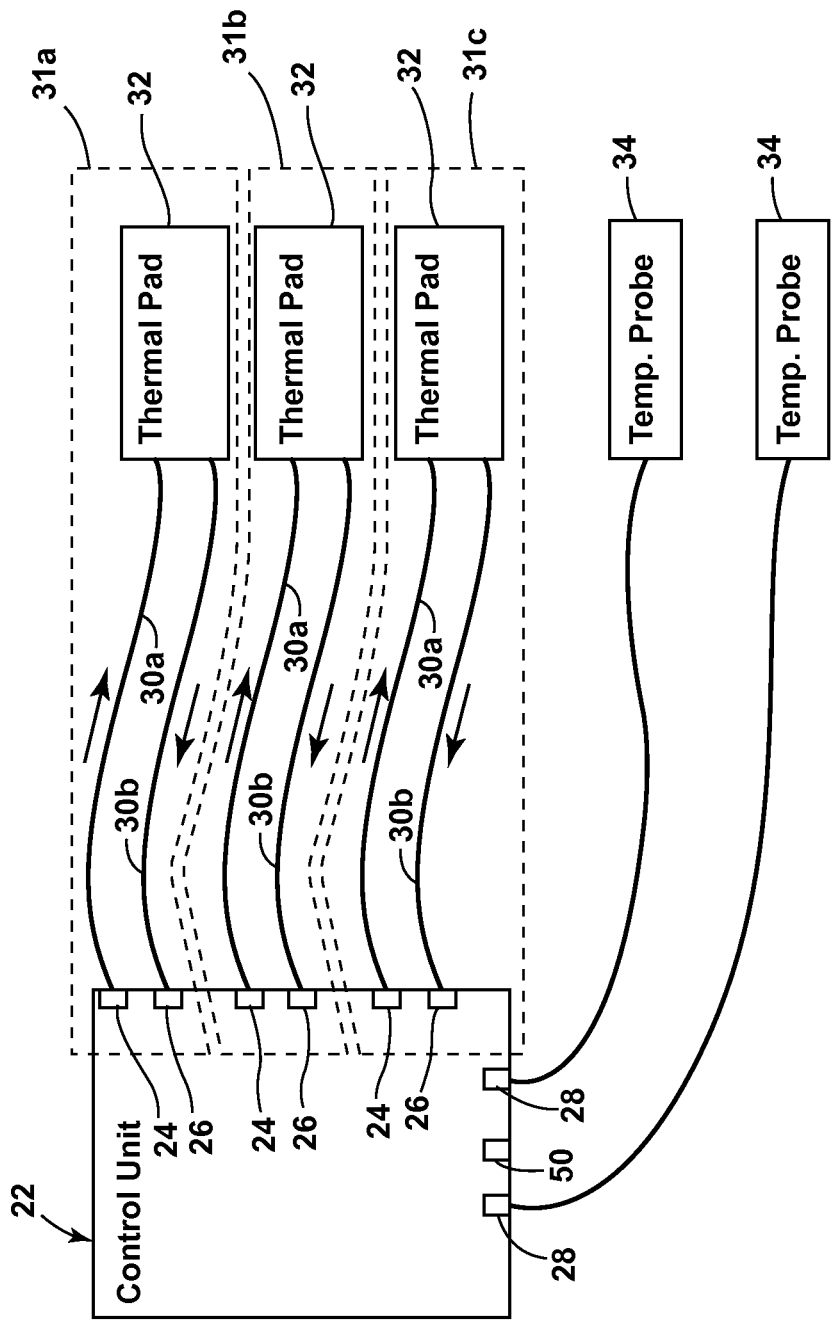
FIG. 1 is a block diagram of a thermal control system according to one aspect of the present invention.

A thermal control system 20 according to one embodiment of the present invention is shown in block diagram form in FIG. 1. Thermal control system 20 includes a thermal control unit 22 having a plurality of fluid outlet ports 24, a plurality of fluid inlet ports 26, and a plurality of patient temperature probe ports 28. The outlet ports 24 define fluid outlets from control unit 22, and each outlet port 24 is adapted to be fluidly coupled to a corresponding fluid supply line or hose 30a that transports a thermal fluid from the thermal control unit 22 to a connected patient thermal therapy device 32, which may be a pad, a blanket, a vest, or other structure. For purposes of the following written description, patient thermal therapy device 32 will be referred to as a thermal pad 32, but it will be understood by those skilled in the art that thermal pad 32 is not limited to pads, but includes any other patient thermal therapy devices. The inlet ports 26 define fluid inlets into control unit 22 and are each adapted to be fluidly coupled to a corresponding fluid return line or hose 30b that returns the thermal fluid from the thermal pad 32 back to the control unit 22. The fluid inside of control unit 22 is therefore pumped by control unit 22 in a circuit that starts at control unit 22, continues through supply lines 30a to the thermal pads 32, and returns back to the control unit 22 by way of return lines 30b.

More specifically, control unit 22 of FIG. 1 circulates the fluid through three fluid circuits 31a, 31b, and 31c. Each fluid circuit 31a, 31b, and 31c is defined by control unit 22, one of the connected thermal pads 32, and the corresponding pair of supply and return lines 30a and 30b. In the embodiment shown in FIG. 1, the fluid that returns to control unit 22 from each return line 30b is mixed in a common manifold (described below), and the temperature of that mixed fluid is controlled to a single desired temperature (which may vary, as will be described more below) by passing it through a heat exchanger 58 (described below). The temperature-controlled fluid is then pumped to each of outlet ports 24, for delivery to each supply line 30a, so that the temperature of the fluid delivered to each outlet port 24 is the same. In this embodiment, each fluid circuit 31a, 31b, and 31c is supplied with fluid at outlet ports 24 that is at the same temperature. In an alternative embodiment, control unit 22 is configured to be able to maintain temperature isolation between one or more of the fluid circuits 31a, 31b, and/or 31c so that fluid of differing temperatures may be delivered from control unit 22 to the outlet ports 24, and thereafter to the thermal pads 32.

In the thermal control unit 22 shown in FIG. 1, there are three inlet ports 26 and three outlet ports 24. By coupling a supply line 30a to each of these three outlet ports 24 and a return line 30b to each of these three return ports 26, temperature controlled fluid can be delivered from control unit 22 to three different thermal pads 32. It will be understood by those skilled in the art that the number of ports 24 and 26 can be varied to include either a smaller or a greater number than the three illustrated in FIG. 1. Still further, it will understood by those skilled in the art that the ports 24, 26 may be provided in various physical configuration and combinations to facilitate the connection and disconnection of the lines 30a, 30b and/or thermal pads 32. As but one example, instead of using a separate pair of ports 24 and 26 for each individual circuit 31a, 31b, and 31c, as shown in FIG. 1, it is possible to modify control unit 22 to include a single multi-tube outlet port 24 and a single multi-tube inlet port 26 that simultaneously couples and de-couples multiple sets of supply lines 30a and return lines 30b to and from control unit 22. Still other variations are possible.

Thermal pads 32 may be any pad, blanket, or other structure adapted to be positioned in either direct contact or close contact with a patient (not shown). By controlling the temperature of the fluid flowing through hoses 30 to thermal pads 32, the temperature of a patient can be controlled via the close contact of the pads 32 with the patient and the resultant heat transfer therebetween. In one conventional configuration, a first thermal pad 32 is wrapped around a patient's torso, while second and third thermal pads 32 are wrapped, respectively, around the patient's right and left legs. Other configurations can be used and, as noted, different numbers of thermal pads 32 may be used with thermal control unit 22, depending upon the number of inlet and outlet ports 26 and 24 that are included with thermal control unit 22. Still further, in some embodiments of thermal control system 20, one or more branching connectors (not shown) may be coupled to a single pair of inlet and outlet ports 26 and 24, if desired, so that multiple lines 30 and multiple thermal pads 32 may be supplied via a single inlet/outlet pair. Such branching, however, reduces the ability of thermal control system 20 to individually monitor the flow and temperature of each thermal pad 32, as will be discussed in greater detail below.

Thermal control system 20 further includes, in the embodiment illustrated in FIG. 1, a plurality of patient temperature probes 34 that are attached to a plurality of different locations of thermal interest on a patient. Such patient temperature probes 34 may be any suitable patient temperature probe that is able to sense the temperature of the patient at the location of the probe. In one embodiment, the patient temperature probes may be conventional Y.S.I. 400 probes marketed by YSI Incorporated of Yellow Springs, Ohio, or probes that are YSI 400 compliant. In other embodiments, different types of probes 34 may be used with thermal control unit 22. Regardless of the specific type of patient temperature probe 34 used in system 20, each temperature probe 34 is connected to a patient temperature probe port 28 positioned on control unit 22. Patient temperature probe ports 28 are in electrical communication with a controller 72 (FIG. 5) that is adapted, in at least some situations, to use the temperature sensed by at least one of the probes 34 in controlling the temperature of the fluid circulated through control unit 22 and pads 32.

Thermal control unit 22 is adapted, in the illustrated embodiment, to operate in a plurality of different modes that are selectable by a user. In a first mode, known as a manual mode, the thermal control unit 22 controls the temperature of the liquid circulating through control unit 22—and thereby the temperature of the fluid delivered to thermal pads 32—so that it matches a target temperature chosen by the user. In this mode, the control unit 22 maintains the liquid at the chosen target temperature regardless of the patient's temperature. Indeed, in the manual mode, control unit 22 may be used without any patient temperature probes 34. In a second mode, known as an automatic mode, the thermal control unit 22 controls the temperature of the liquid circulating through control unit 22 in such a manner that a target patient temperature is achieved and/or maintained. In this automatic mode, at least one patient temperature probe 34 must be coupled to control unit 22 so that control unit 22 knows the patient's current temperature. In the automatic mode, control unit 22 does not necessarily adjust the temperature of the circulating fluid to maintain a constant temperature, but instead makes the necessary temperature adjustments to the fluid in order to effectuate the desired patient temperature.

As noted, when thermal control unit 22 is used in the automatic mode, at least one patient temperature probe 34 must be coupled to control unit 22. However, as shown in FIG. 1, more than a single patient temperature probe 34 may be coupled to control unit 22. In the embodiment shown in FIG. 1, control unit 22 is configured to allow a user to select which of the multiple patient temperature probes 34 are to be used by the control unit for effectuating the desired patient temperature control. That is, the user can tell control unit 22 which of the two (or more) patient temperature readings the control unit 22 is supposed to control. The non-selected patient temperature reading is simply displayed by control unit 22 for informational purposes, but is not otherwise used in controlling the temperature of the liquid circulating through control unit 22.

In an alternative embodiment, control unit 22 allows the user to select both temperature probes 34 to be used for effectuating the desired patient temperature control, or all of the temperature probes 34 (if control unit 22 is configured to accept more than two patient temperature probes 34). In such embodiments, control unit 22 is adapted to utilize the temperature readings from the multiple temperature probes 34 by mathematically combining them. The mathematical combination may be a simple average of the multiple temperature readings, a weighted average based on the location of the probes 34 on the patient's body (or some other factor), or some other type of mathematical combination that is user-controllable. Alternatively, if control unit 22 is configured to output fluid at different temperatures to different ones of circuits 31, control unit 22 may use the temperature readings from the multiple probes 34 without mathematically combining them, such as, but not limited to, using a first probe 34 reading for controlling a first one of the fluid circuits 31, using a second probe 34 reading for controlling a second one of the fluid circuits 31, etc. Still other variations are possible.

Figure 2:
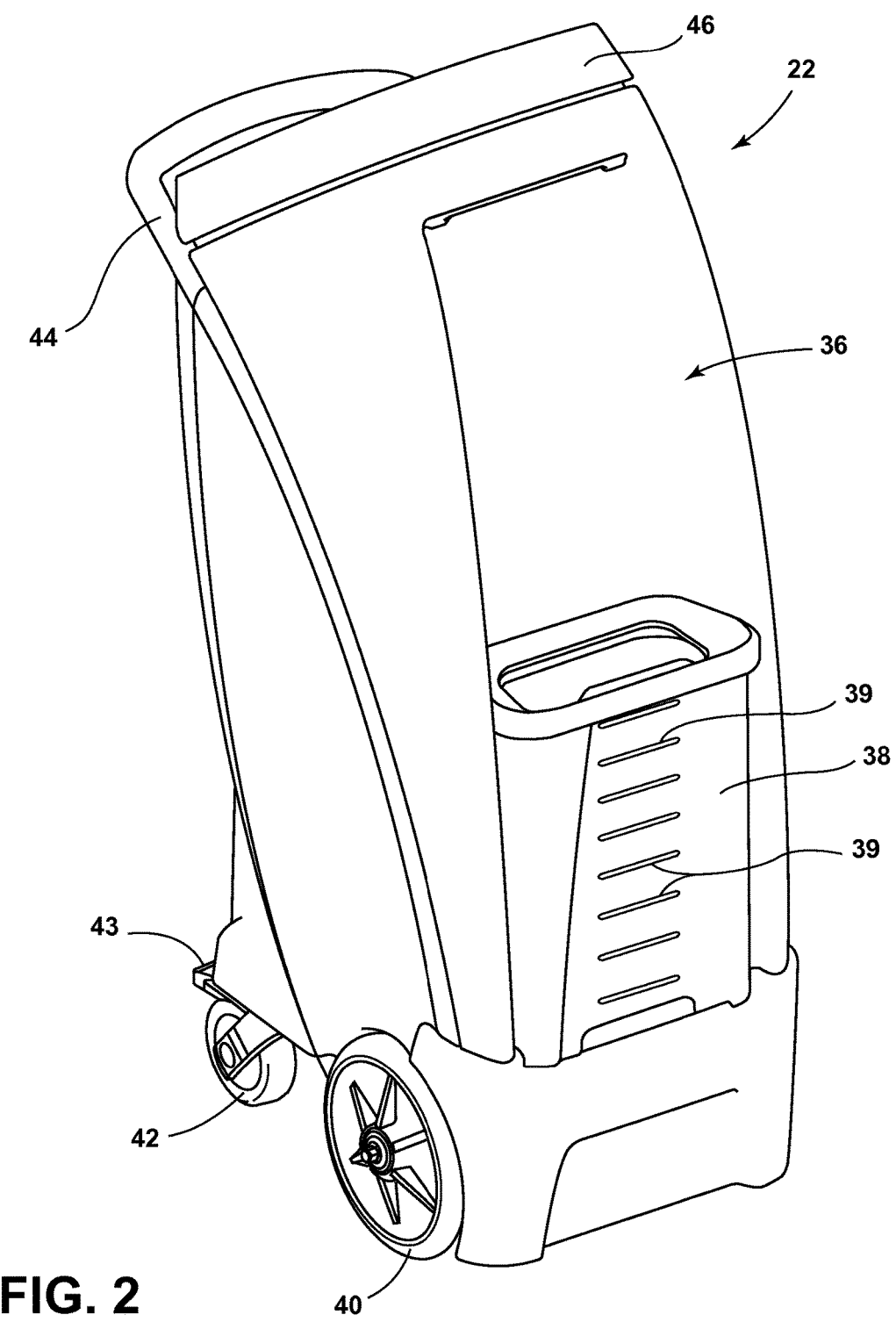
FIG. 2 is a perspective view of one embodiment of a thermal control unit that may be used in the thermal control system of FIG. 1.
Figure 3:
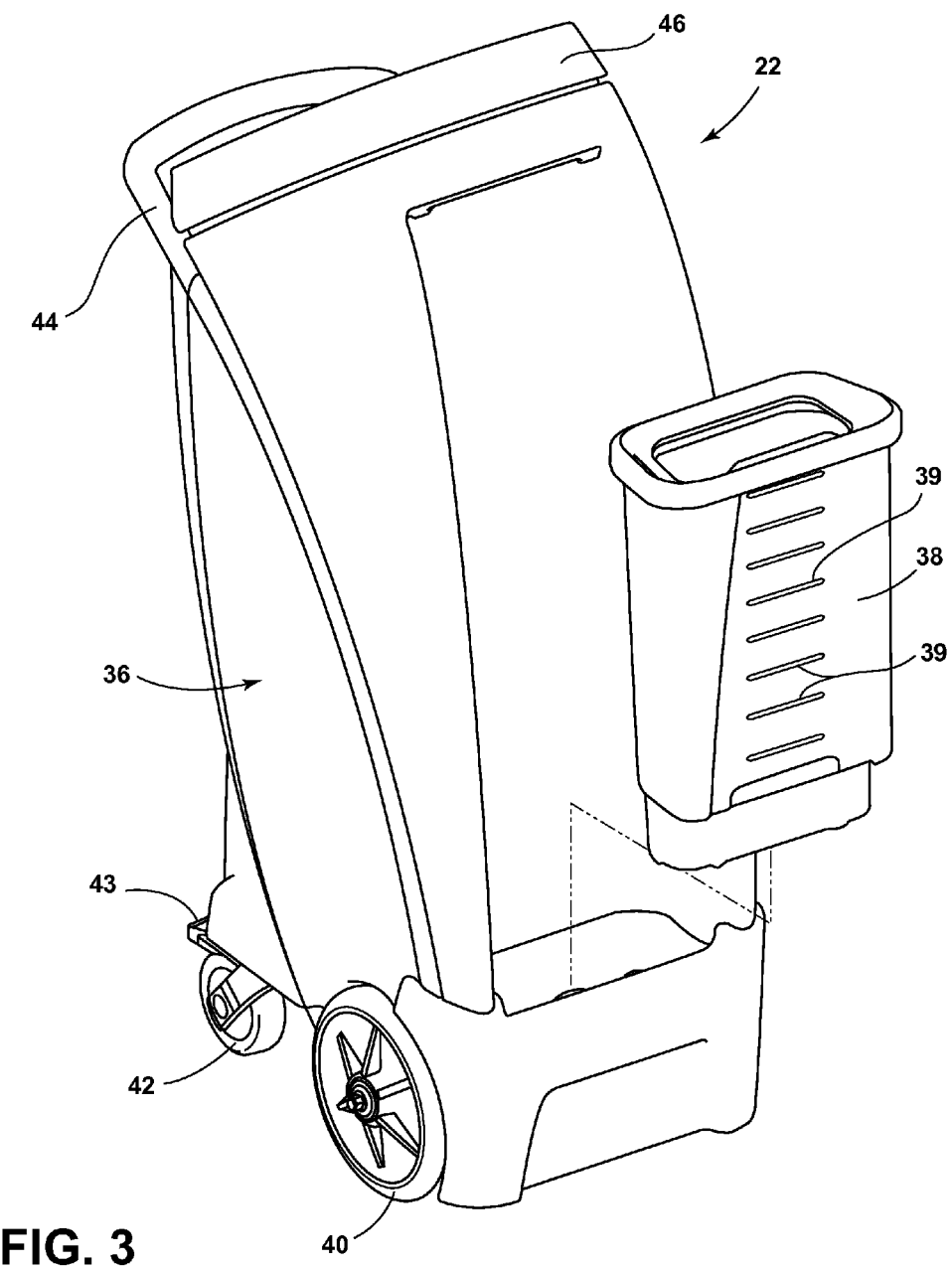
FIG. 3 is a perspective view of the thermal control unit of FIG. 2 shown with a fluid reservoir removed.
Figure 4:
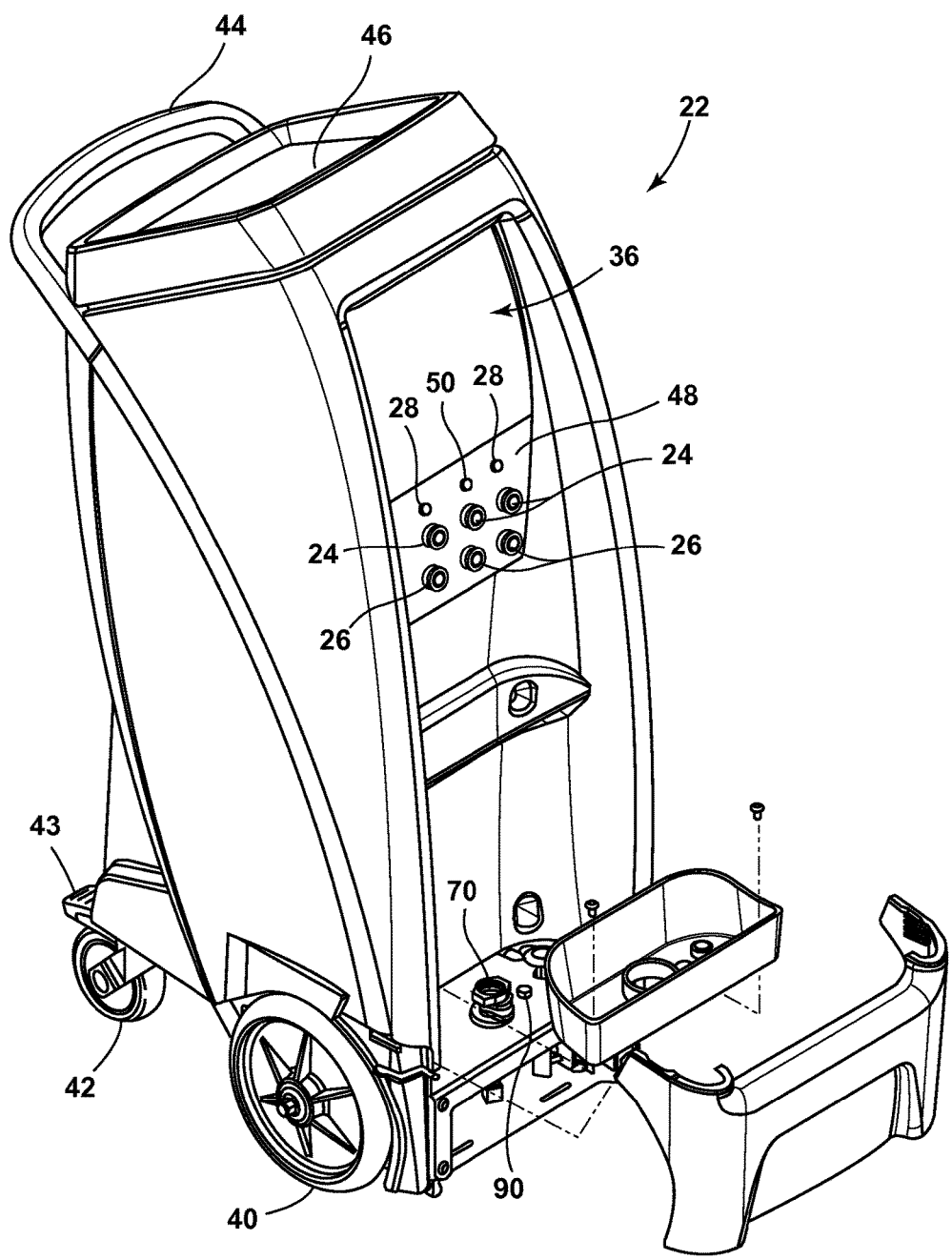
FIG. 4 is a perspective view of the thermal control unit of FIG. 2 shown with a bumper and front cover panel detached.

One embodiment of thermal control unit 22 is shown in perspective view in FIGS. 2-4. Thermal control unit 22 includes a main body 36 to which a removable reservoir 38 may be coupled and uncoupled. Removable reservoir 38 is configured to hold the fluid (typically water, although other liquids may be used) that is to be circulated through control unit 22 and the one or more thermal pads 32. By being removable from thermal control unit 22, reservoir 38 can be easily carried to a sink or faucet for filling and or dumping of the water or other fluid. This allows users of system 20 to more easily fill control unit 22 prior to its use, as well as to drain unit 22 after use. Removable reservoir 38 further includes, in the illustrated embodiment, volume gradations 39 on its outside that provide a visual indication to the user of how much fluid (or other liquid) is contained within reservoir 38. The individual gradations 39 may correspond to any appropriate measure of fluid volume, such as, but not limited to, liters, gallons, quarts, fractions thereof, or any other units of fluid volume.

Control unit 22 further includes a pair of non-caster wheels 40 and a pair of caster wheels 42. At least one caster wheel includes a toggle brake 43 that is activated by pushing down on it once and deactivated by pushing down on it a second time. When braked, movement of control unit 22 is restricted. Control unit 22 further includes a handle 44 attached to main body 36. Handle 44 is provided for grasping by a user when transporting control unit 22 to different locations. Still further, control unit 22 includes a control panel 46 positioned at the top end of main body 36. Control panel 46, as will be described in greater detail below, includes a touchscreen for controlling the various aspects and functionalities of control unit 22.

Main body 36 of control unit 22 further includes a port panel 48 having a plurality of ports positioned thereon (shown in FIG. 4). More specifically, port panel 48 includes the three inlet ports 26, the three outlet ports 24, and a pair of patient temperature probe ports 28. Still further, in the embodiment illustrated in FIG. 4, a patient temperature output port 50 is provided. Patient temperature output port 50 allows a patient temperature probe from another medical device or monitor to be coupled thereto and to receive the same patient temperature reading that control unit 22 is receiving from the patient temperature probe 34. If control unit 22 is connected to multiple patient temperature probes 34, patient temperature output port 50 will output the temperature of the probe 34 selected by the user using control panel 46. That is, a user is able to designate which of the two patient temperature probe ports 28 is to be considered the primary port. The patient temperature that is detected by the probe 34 that is plugged into the probe port 28 that has been designated as the primary port will be forwarded to patient temperature output port 50. Patient temperature output port 50 therefore allows other devices to utilize the temperature readings gathered from a patient temperature probe 34 so that fewer patient temperature probes need to be coupled to the patient, thereby reducing cable clutter, as well as reducing the potential space limitations on the patient's body.

Figure 5:
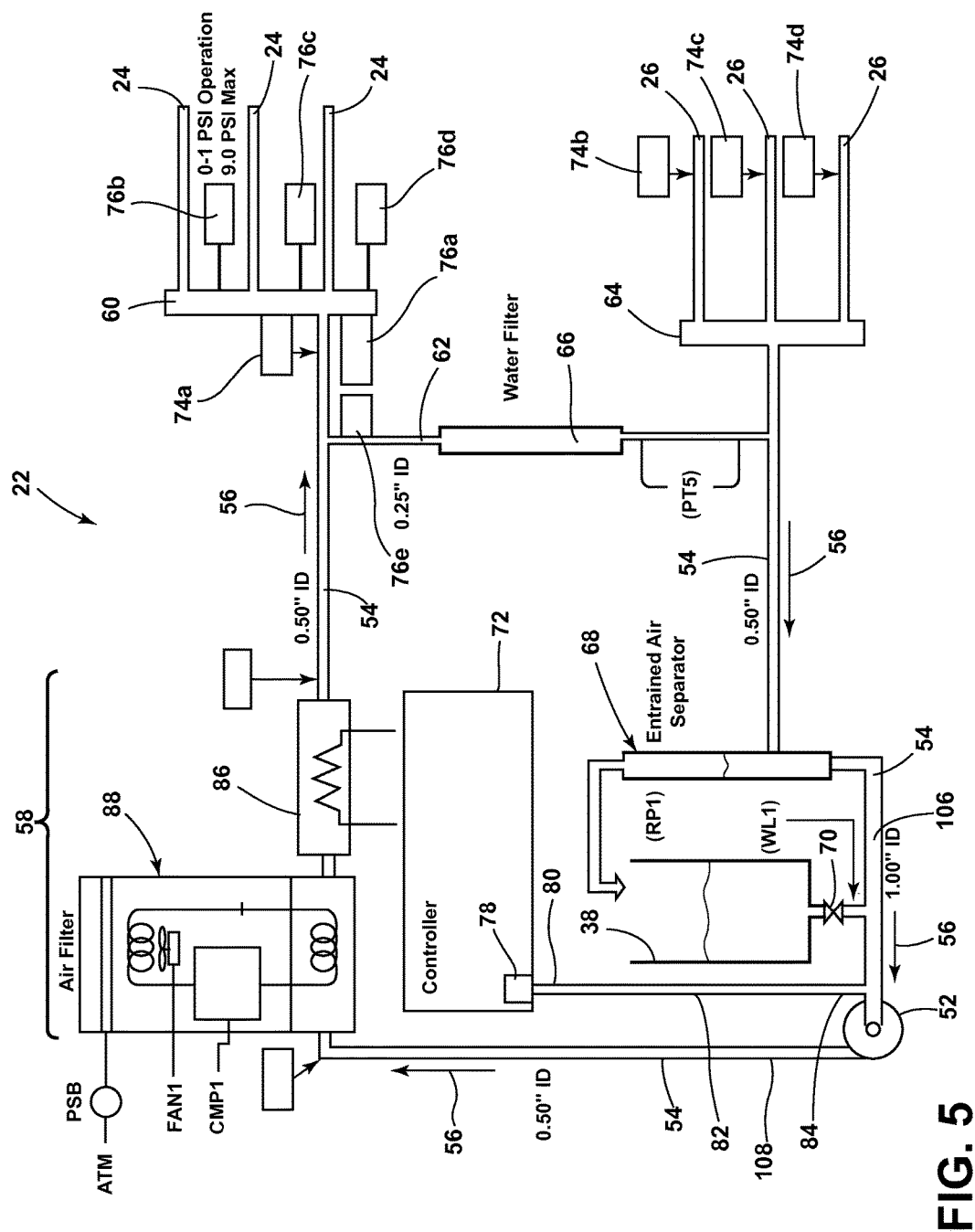
FIG. 5 is a diagram of an illustrative fluid circulation arrangement that may be used in any of the thermal control units disclosed herein.

FIG. 5 illustrates a diagram of the internal construction of thermal control unit 22. As seen in FIG. 5, thermal control unit 22 includes a pump 52 for circulating fluid through a circulation channel 54. Pump 52, when activated, circulates the fluid through circulation channel 54 in the direction of arrows 56 (clockwise in FIG. 5). Starting at pump 52, the circulating fluid first passes through a heat exchanger 58 where it is delivered to an outlet manifold 60 having the plurality of outlet ports 24. A bypass line 62 is fluidly coupled to outlet manifold 60 and an inlet manifold 64. Bypass line 62 allows fluid to circulate through circulation channel 54 even in the absence of any thermal pads 32 or lines 30 being coupled to any of outlet and inlet ports 24 and 26. In the illustrated embodiment, bypass line 62 includes an optional filter 66 that is adapted to filter the circulating fluid. If included, filter 66 may be a particle filter adapted to filter out particles within the circulating fluid that exceed a size threshold, or filter 66 may be a biological filter adapted to purify or sanitize the circulating fluid, or it may be a combination of both.

Inlet manifold 64 includes the plurality of inlet ports 26 that receive fluid returning from the one or more connected thermal pads 32. The incoming fluid from inlet ports 26, as well as the fluid passing through bypass line 62, travels back toward the pump 52 into an air separator 68. Air separator 68 includes a generally vertical tube that is open at its top end to atmospheric pressure. Any air bubbles that are entrained in the circulating fluid will naturally rise up through air separator 68 and be vented to the atmosphere. After passing through air separator 68, the circulating fluid flows past a valve 70 positioned beneath fluid reservoir 38 and back to pump 52.

Thermal control unit 22 further includes controller 72 (FIG. 5) that is contained within main body 36 and in electrical communication with a variety of different sensors and/or actuators. More specifically, controller 72 is in electrical communication with pump 52, heat exchanger 58, and control panel 46. While not illustrated in FIG. 5, controller 72 is further in communication with first, second, third, and fourth temperature sensors 74a, b, c, and d, respectively, as well as with first, second, third, fourth, and fifth pressure sensors 76a, b, c, d, and e, respectively (or turbine flow sensors, if used, as discussed below). Controller 72 is also in communication with an air pressure sensor 78 that is positioned in gaseous communication with a top end 80 of a level sensing tube 82. Level sensing tube 82 is generally vertical and includes a lower end 84 that is in fluid communication with fluid circulation channel 54.

Controller 72 includes any and all electrical circuitry and components necessary to carry out the functions and algorithms described herein, as would be known to one of ordinary skill in the art. Generally speaking, controller 72 may include one or more microcontrollers, microprocessors, and/or other programmable electronics that are programmed to carry out the functions described herein. It will be understood that controller 72 may also include other electronic components that are programmed to carry out the functions described herein, or that support the microcontrollers, microprocessors, and/or other electronics. The other electronic components include, but are not limited to, one or more field programmable gate arrays, systems on a chip, volatile or nonvolatile memory, discrete circuitry, integrated circuits, application specific integrated circuits (ASICs) and/or other hardware, software, or firmware, as would be known to one of ordinary skill in the art. Such components can be physically configured in any suitable manner, such as by mounting them to one or more circuit boards, or arranging them in other manners, whether combined into a single unit or distributed across multiple units. Such components may be physically distributed in different positions in thermal control unit 22, or they may reside in a common location within thermal control unit 22. When physically distributed, the components may communicate using any suitable serial or parallel communication protocol, such as, but not limited to, CAN, LIN, Firewire, I-squared-C, RS-232, RS-485, universal serial bus (USB), etc.

As illustrated in FIG. 5, heat exchanger 58 includes both a heater 86 and a chiller 88. Heat exchanger 58 is therefore capable of both cooling the circulating liquid and heating the circulating liquid. In some instances, where precise temperature control is desired, such heating and cooling may occur at the same time. That is, the circulating fluid may be sequentially both heated and cooled, with the latter heating or cooling occurring if the first temperature adjustment overshoots the intended target temperature. In other embodiments, heat exchanger 58 may include only a chiller 88 or only a heater 86, depending upon the desired type of temperature control. In the illustrated embodiment where heat exchanger 58 includes both a chiller 88 and a heater 86, both heater 86 and chiller 88 are in communication with, and under the control of, controller 72.

Controller 72 uses the outputs of temperature sensors 74a, b, c, and d to control the temperature of the circulating fluid. That is, controller 72 uses the outputs of temperature sensors 74a, b, c, and d to control heat exchanger 58 such that the fluid circulating therethrough has its temperature adjusted (or maintained) in accordance with the operating mode (manual or automatic) selected by the user of thermal control unit 22. In one embodiment, controller 72 controls the temperature of the circulating fluid by using both an output temperature value (as measured by temperature sensor 74a) and a return temperature value (as determined from a mathematical combination of the readings from sensors 74b, c, and/or d). More specifically, controller 72 averages the temperature readings from sensors 74b, c, and d (or a subset of these three sensors if fewer than all three return ports 26 are being utilized) to generate the return temperature value. Controller 72 uses the return temperature value as the measured variable in implementing a closed loop proportional-integral (PI) controller for controlling the circulating fluid temperature. The target temperature of the circulating fluid is supplied either by a user (manual mode) or automatically by controller 72 (in automatic mode) based on a desired patient temperature and the current patient temperature (as determined from one of probes 34). Controller 72 thus compares the measured return temperature value to the target temperature and, if different, makes corresponding adjustments in the temperature (via heat exchanger 58) in order to change the current temperature to the target temperature. When carrying out this control using the PI controller, controller 72, in one embodiment, uses the output temperature value from temperature sensor 74a to adjust the limits of integration of the PI controller. Other types of controllers may be used in other embodiments for adjusting the temperature of the circulating fluid.

Controller 72 is further configured to display each of the temperatures sensed by temperature sensors 74b, 74c, and 74d. That is, controller 72 is configured to display to the user the individual temperature readings associated with the fluid returning to each of the inlet ports 26. Because each inlet port 26 may be attached to a different thermal pad 32, which in turn is likely positioned at a different location on the patient's body, the returning fluid from each thermal pad 32 may be at a different temperature. Further, it may be useful for a caregiver to know which of the multiple thermal pads 32 is responsible for the largest, or smallest, temperature change relative to the temperature of the outgoing fluid, and thereby the largest or smallest amount of heat transfer with respect to the patient. Thermal control unit 22 therefore provides the user with individualized temperature information for each of the multiple inlet ports. Further, controller 72 is configurable to also display the outgoing fluid temperature on control panel 46, as sensed by outgoing fluid temperature sensor 74a.

Controller 72 utilizes the data outputs from fluid pressure sensors 76a, b, c, d, and e in order to determine the flow rate or amount of flow volume. As would be known to one of ordinary skill in the art, the flow volumes can be calculated based upon the difference in pressures between pressure sensor 76a and each of the outgoing pressure sensors 76b, 76c, and 76d (and/or the bypass pressure sensor 76e) as well as the known orifice sizes of the outlet ports 24 (and/or the bypass line 62). More specifically, controller 72 is configured to individually calculate the flow rate of fluid exiting out each of the three outlet ports 24, as well as the flow rate of fluid passing through bypass line 62. Controller 72 calculates the flow rate through a first outlet port 24 by using the difference in pressure between pressure sensor 76a and 76b (as well as other data, such as orifice sizes). Controller 72 calculates the flow rate through a second outlet port 24 by using the difference in pressure between pressure sensor 76a and 76c (as well as other data). And controller 72 calculates the flow rate through a third outlet port 24 by using the difference in pressure between pressure sensor 76a and 76d (as well as other data). Still further, controller 72 calculates the flow rate through the bypass line 62 by using the difference in pressure between pressure sensor 76a and 76e (as well as other data). Controller 72 is also configured to display each of the individual outlet port flow volumes on control panel 46 so that a user of control unit 22 will know the amount of fluid flowing to each individual thermal pad 32. In some embodiments, controller 72 is also configured to display the amount of fluid flowing through bypass line 62 as well.

Controller 72 uses the flow data in its closed-loop feedback control of heat exchanger 58. In one embodiment, controller 72 uses a proportional-integral control loop (PI control). In other embodiments, controller 72 can be adapted to use a proportional-integral-derivative control loop (PID control). In still other embodiments, controller 72 may simply use proportional control with no integral or derivative terms. Regardless of the specific type of control loop used, controller 72 uses the information from the pressure sensors 76a-e, as well as the temperature sensors 74a-d in determining the control commands that are issued to heat exchanger 58.

In other embodiments, pressure sensors 76a, b, c, d, and/or e are replaced by turbine sensors that directly measure flow rates. Still further, in other embodiments, the positions of pressure sensors 76a, b, c, d, and/or e (or turbine flow sensors, if used) are changed from that shown in FIG. 5. For example, in one embodiment, outlet manifold pressure sensor 76a is replaced with a turbine flow sensor positioned just downstream of pump 52. In still another embodiment, pressure sensors 76b, c, and d (whether implemented as pressure sensors or turbine flow sensors) are positioned at inlet ports 26 rather than outlet ports 24. Still other variations are possible. In still another embodiment, both pressure sensors 76 and turbine flow sensors are used to measure fluid flow rates.

Figure 22:
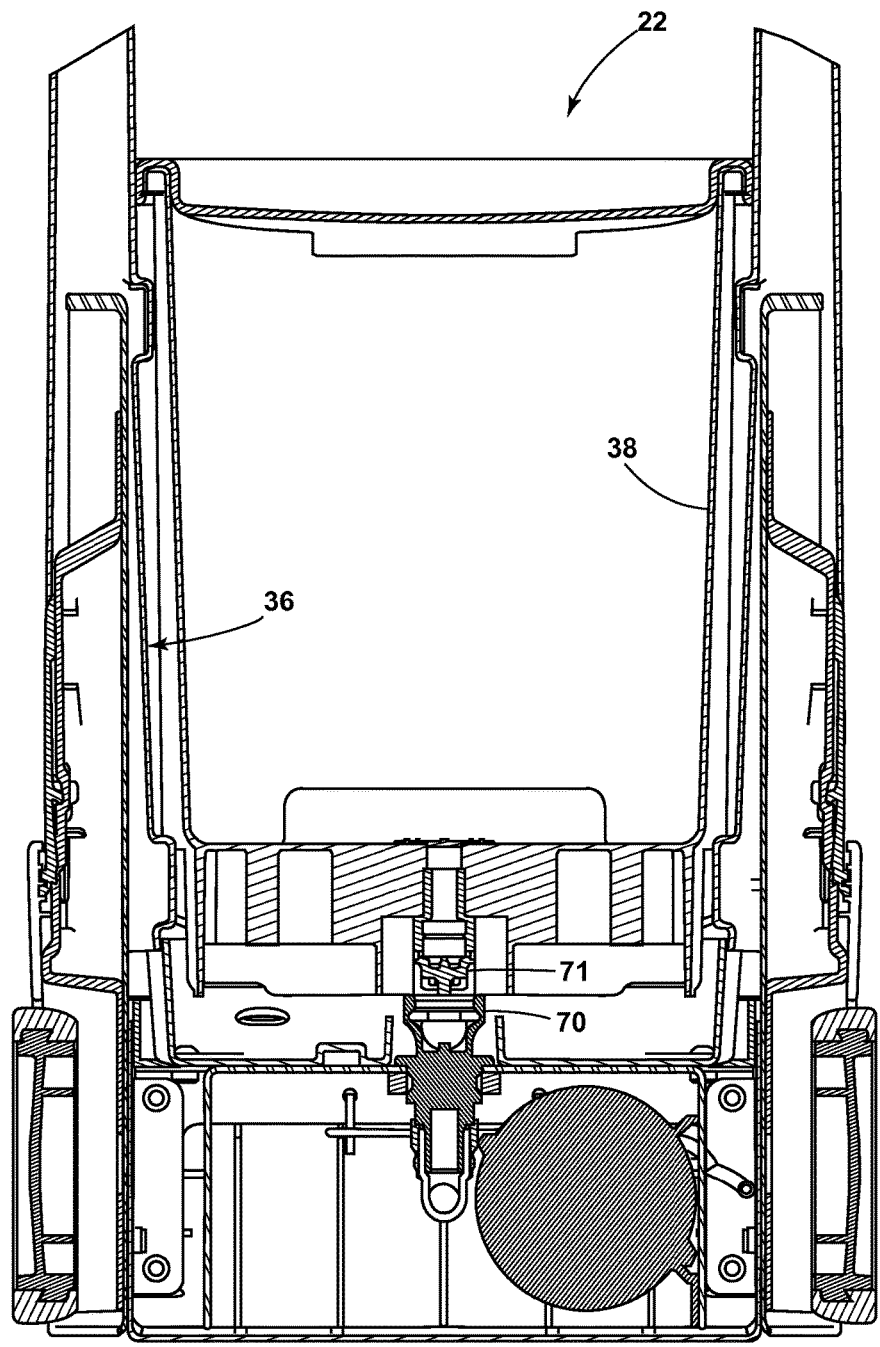
FIG. 22 is a sectional rear elevational view of the fluid reservoir and thermal control unit shown coupled together.

Removable reservoir 38 includes on its bottom a valve 71 (FIG. 22) that automatically cooperates with valve 70 within control unit 22 when reservoir 38 is inserted into the position shown in FIGS. 2 and 22. More specifically, valve 71 automatically closes when reservoir 38 is removed from control unit 22 so that any fluid that is contained within it, or that is added to it, will not leak out of reservoir 38. Likewise, valve 70 automatically closes when reservoir 38 is lifted out of control unit 22 so that any fluid in the control unit 22 does not leak out of it. When removable reservoir 38 is inserted into control unit 22, both valve 70 and valve 71 cooperate with each other to both open. This automatic opening allows fluid to flow either into or out of control unit 22, depending upon what fluid, if any, is already present within control unit 22 and the relative pressure of that fluid compared to any fluid that is contained within reservoir 38. Valves 70 and 71 may be commercially available valves, such as are available from Colder Products Company of St. Paul, Minn., or from other suppliers.

Control unit 22 is configured such that removable reservoir 38 can be removed while thermal therapy is being delivered to a patient without any interruption in that thermal therapy. That is, controller 72 will continue to control the delivery of temperature controlled fluid to one or more thermal pads 32 even if reservoir 38 is removed from unit 22. Controller 72 will provide an indication to a user that reservoir 38 has been removed (via a sensor discussed below), but this will not interrupt the delivery of temperature controlled fluid to a patient via pads 32. In this manner, reservoir 38 can be removed and carried to a sink or other location for adding or draining water, or other fluid, to reservoir 38 simultaneously with the delivery of thermal therapy to a patient. If reservoir 38 is inserted back into control unit 22 during this delivery of thermal therapy to the patient, the reservoir valve and valve 70 will automatically open and whatever fluid within reservoir 38, if any, will be put in fluid communication with the fluid circulating through control unit 22.

When reservoir 38 is first filled and control unit 22 is used for the very first time, the coupling of reservoir 38 to control unit 22 will cause the reservoir valve and valve 70 to both open, as noted, thereby allowing the fluid within reservoir 38 to flow out and into a portion of circulating channel 54. More specifically, fluid will flow into pump 52, a portion of level sensing tube 82, and a portion of air separator 68. In the illustrated embodiment, the fluid will not flow into either outlet manifold 60 or inlet manifold 64 as those are positioned at a higher elevation than fluid reservoir 38 within control unit 22. Only when pump 52 is activated will fluid be pumped to these manifolds 60 and 64.

When pump 52 is activated, it will pump fluid throughout circulating channel 54 and any connected thermal pads 32. The fluid needed to fill the spaces in circulating channel 54 and thermal pads 32 that were previously occupied by air is drawn from reservoir 38. Once the entire system (circulating channel 54, manifolds 60 and 64, and any connected pads 32) is filled with fluid drawn from reservoir 38, any remaining fluid within reservoir 38 will remain within reservoir 38 and be substantially outside of the circulating loop of fluid. That is, the fluid within reservoir 38 will be substantially isolated from the circulating fluid such that temperature changes made to the circulating fluid will have little to no impact on the temperature of the fluid within reservoir 38. In this manner, it is not necessary to expend the extra time and energy that would otherwise be necessary to bring the volume of fluid within reservoir 38 to the desired temperature. Instead, any temperature adjustments made to the fluid are made only to the portion of the fluid that is circulating, thereby avoiding unnecessary expenditures of energy and time on heating or cooling fluid that does not circulate to the thermal pads. In this manner, thermal control unit 22 operates as a tank-less thermal control unit that has a faster response time than many prior art thermal control units. That is, thermal control unit 22 is able to bring the circulating fluid to a desired temperature quicker and/or with less energy than thermal control units that include a tank and greater amounts of fluid within the thermally controlled circuit.

Figure 6:
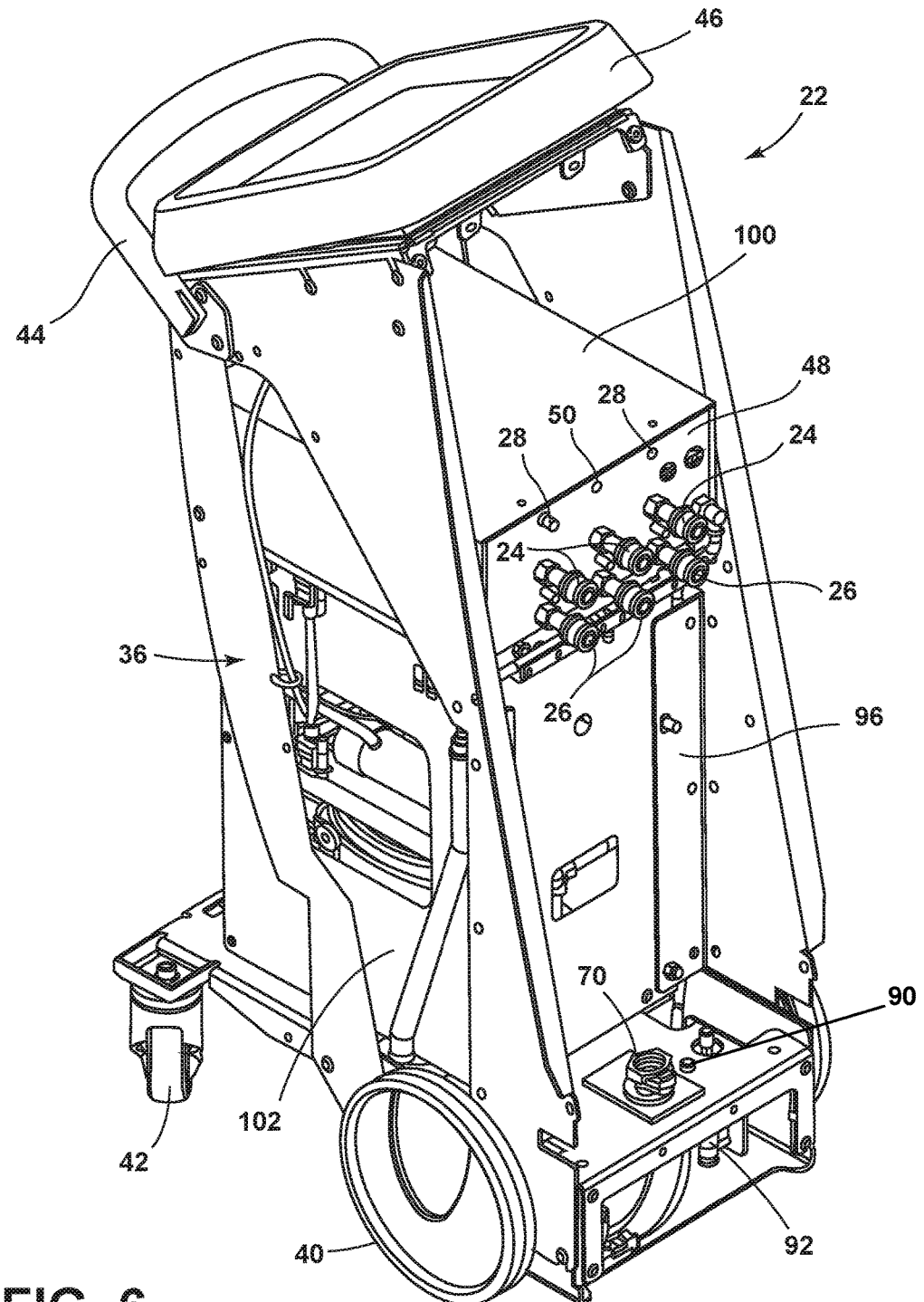
FIG. 6 is a perspective, partially disassembled, view of the thermal control unit of FIG. 2 illustrating a temperature control assembly and control panel mounted to a frame of the thermal control unit.
Figure 7:
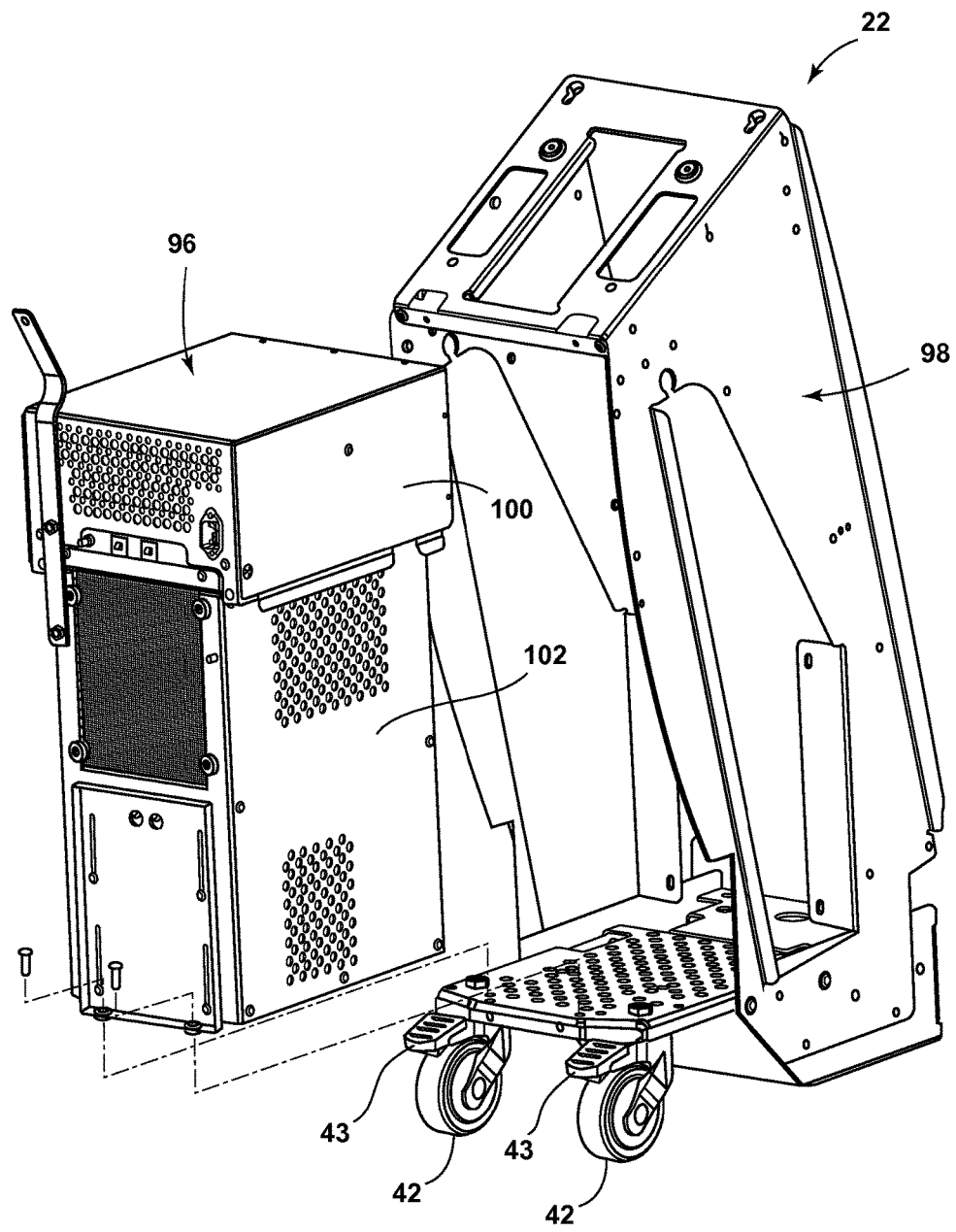
FIG. 7 is a perspective view of the temperature control assembly of FIG. 6 removed from the thermal control unit frame.

When pump 52 is deactivated after having been activated, the fluid within circulating channel 54 will drain downward due to gravity into the lower regions of circulating channel 54, as well as partially returning into reservoir 38, when attached. Any fluid within thermal pads 32 will also return to the lower regions of circulating channel 54 provided the pads 32 are positioned at a height that is greater than the height of inlet ports 26 so that gravity may pull the fluid downward out of the pads 32 and through inlet ports 26. The deactivation of the pump 52 will therefore return a portion of the circulating fluid to reservoir 38 while leaving another portion of the circulating fluid in the bottom areas of circulating channel 54. In order to more completely remove the fluid from circulating channel 54, a drain 92 (FIG. 6) can be opened to further drain the fluid out of control unit 22, if desired, as will be discussed in greater detail below.

Thermal control unit 22 is further in electrical communication with a reservoir sensor 90 (FIG. 6) that is adapted to electrically detect the presence or absence of reservoir 38. Reservoir sensor 90 may be any suitable sensor for detecting the absence and presence of reservoir 38. In the illustrated embodiment, reservoir sensor 90 is a Reed switch that is adapted to detect the absence or presence of a magnet (not shown) integrated into the bottom of the reservoir 38 at a location that aligns with sensor 90 (when reservoir 38 is coupled to unit 22). Reservoir sensor 90 communicates the presence or absence of reservoir 38 to controller 72 which, in turn, is configured to display that information on control panel 46, as well as to issue alerts or warnings if the user attempts to implement a function that is dependent upon the presence of reservoir 38 and sensor 90 is detecting its absence.

Figure 8:
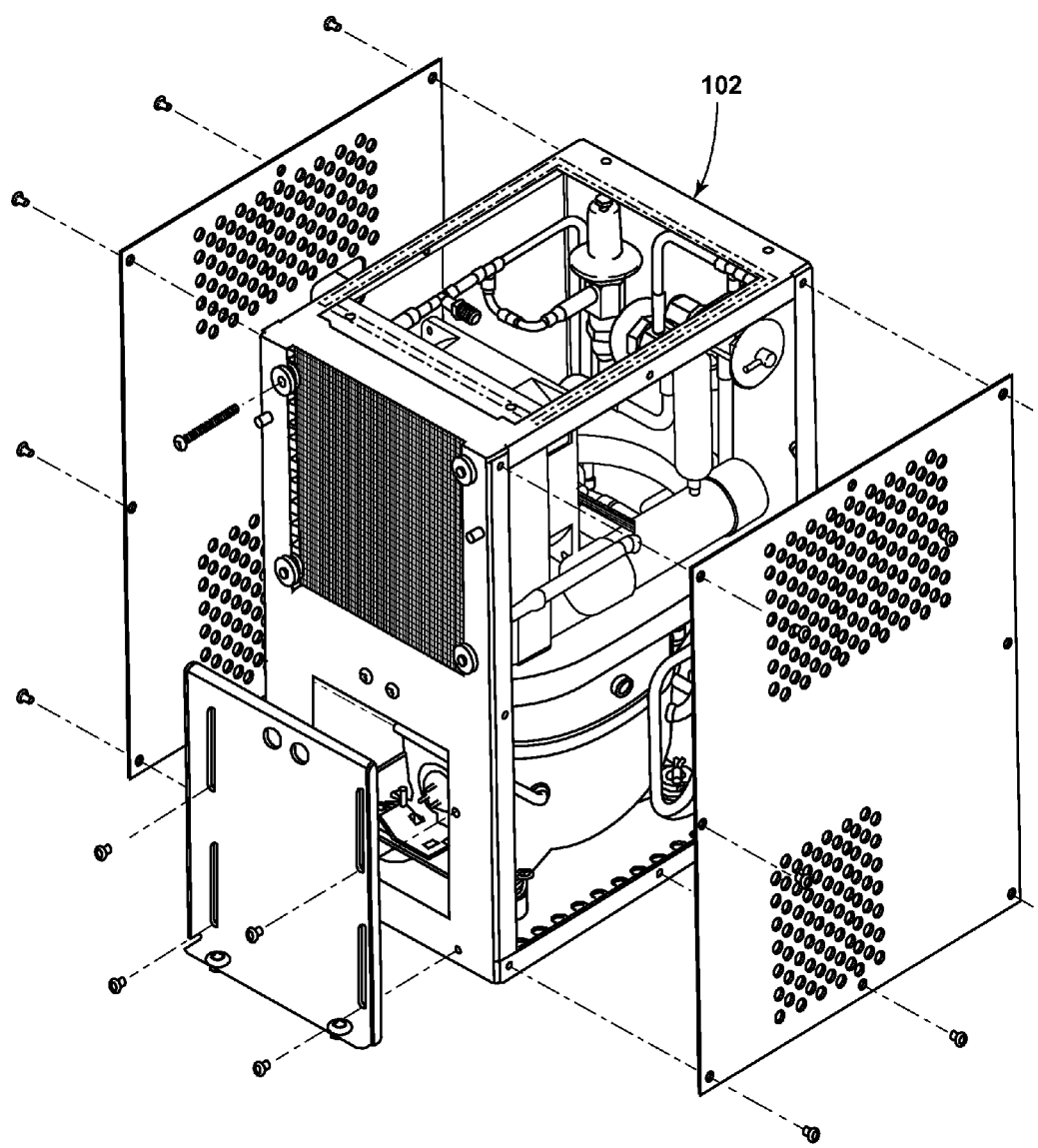
FIG. 8 is a partially exploded view of the temperature control assembly of FIGS. 6 and 7.
Figure 9:
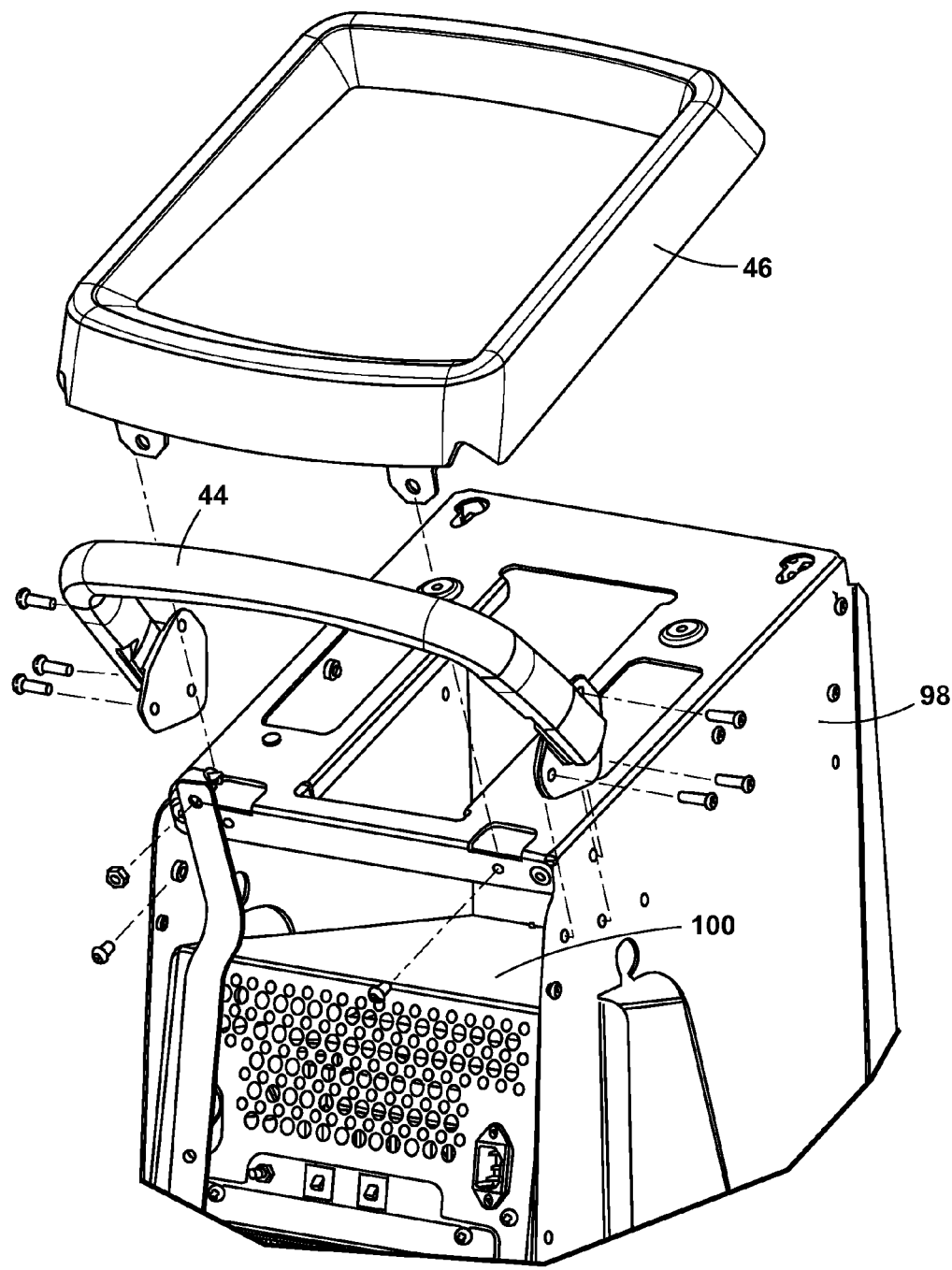
FIG. 9 is a partially exploded view of a control panel of the thermal control unit of FIG. 2.

As shown in more detail in FIGS. 6-9, thermal control unit 22 includes within main body 36 a temperature control assembly 96. As shown in more detail in FIG. 7, temperature control assembly 96 is removable from a frame 98 within thermal control unit 22. Temperature control assembly 96 is made up of a control box assembly 100 and a heat exchange assembly 102 (FIG. 8). Control box assembly 100 includes controller 72 as well as various other components, as will be described in more detail below. Heat exchange assembly 102 includes heat exchanger 58.

Figure 10:
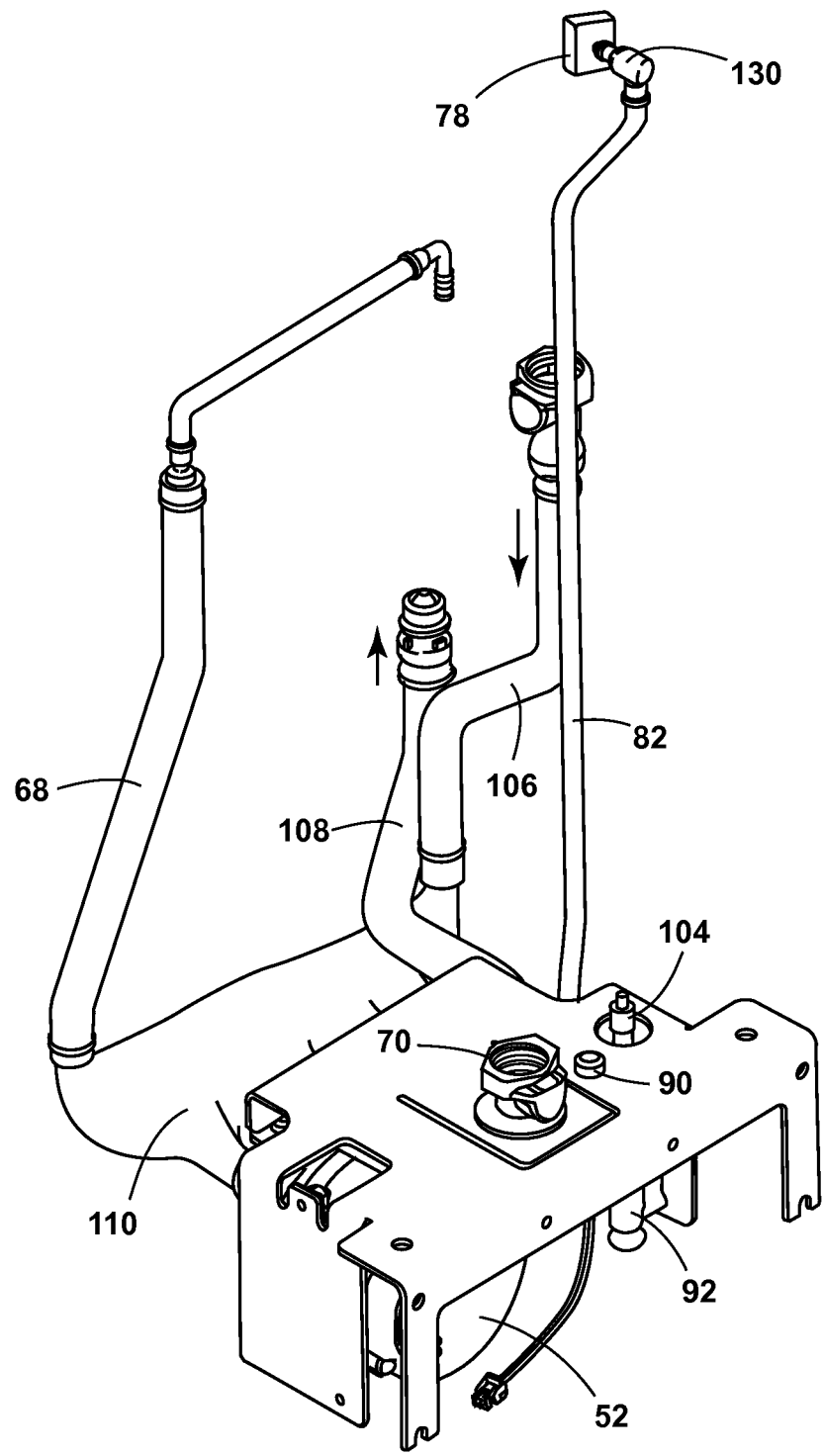
FIG. 10 is a perspective view of a fluid assembly of the thermal control unit of FIG. 2.

FIG. 10 illustrates a bottom portion of the main body 36 of thermal control unit 22. This bottom portion includes valve 70 for interacting with removable reservoir 38, as well as reservoir sensor 90 for detecting the absence or presence of reservoir 38. In addition, this bottom portion includes an automatic drain plug 104, air separator 68, level sensing tube 82, a pump inlet tube 106, a pump outlet tube 108, and a lower fluid chamber 110. Pump inlet tube 106 and pump outlet tube 108, which are also shown in FIG. 5, each define a portion of circulation channel 54. Pump inlet tube 106 receives fluid that returns back from the thermal pads 32 into inlet manifold 64, as well as fluid that flows through bypass line 62. Pump outlet tube 108 connects to, and delivers fluid to, heat exchanger 58, which is housed within heat exchange assembly 102.

Figure 11:
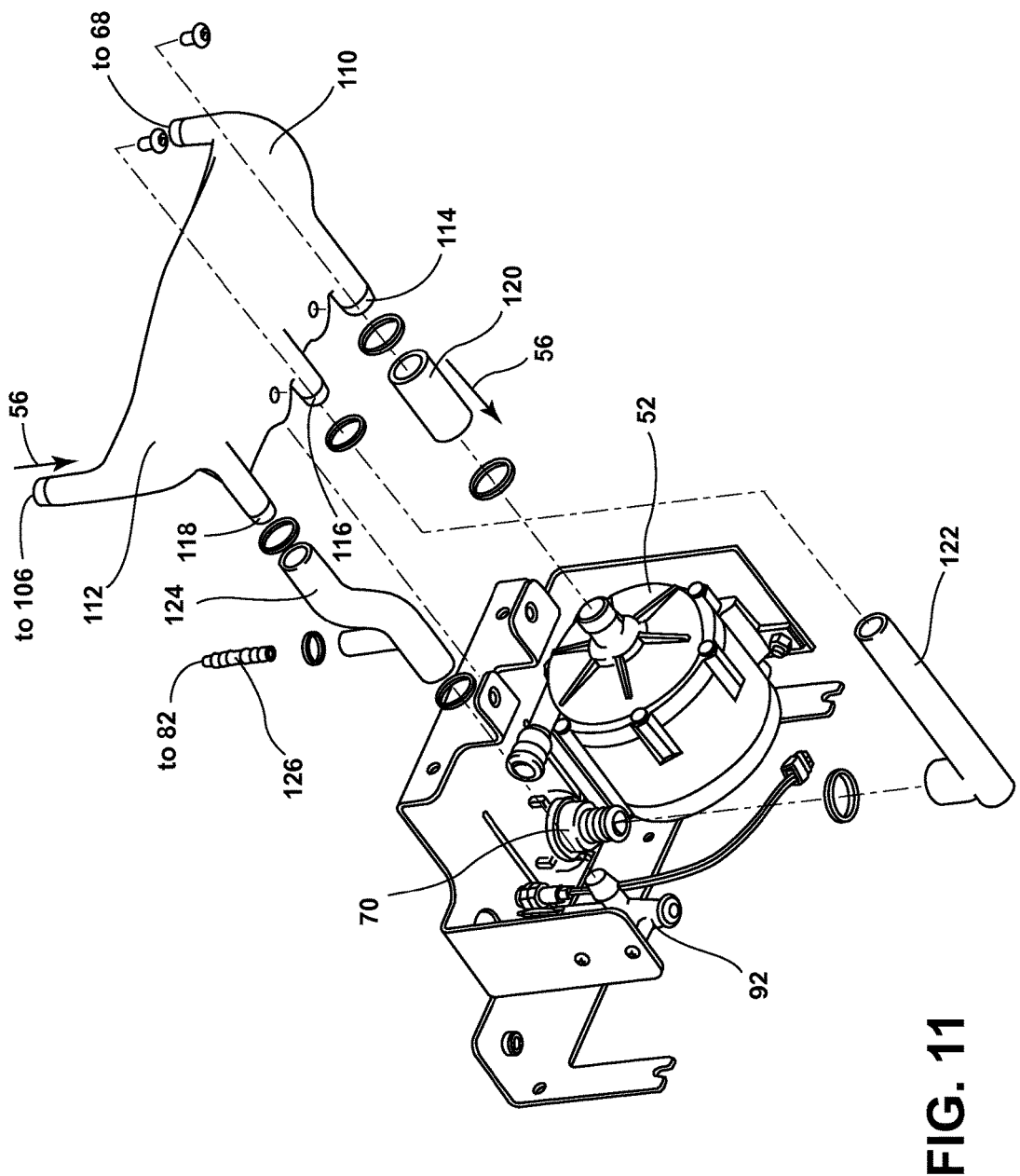
FIG. 11 is a perspective exploded view of a base section of the fluid assembly of FIG. 10.

Lower fluid chamber 110 is illustrated in more detail in FIG. 11 and includes a central body portion 112, a pump port 114, a fill port 116, and a drain port 118. Pump port 114 is fluidly connected to pump 52 by way of a connection pipe 120 that delivers fluid to pump 52 (fluid moves in the direction of arrows 56). Fill port 116 is fluidly connected by a fill pipe 122 to valve 70 and the contents of reservoir 38 (when coupled to control unit 22). Drain port 118 is fluidly connected to a drain pipe 124 that is, in turn, fluidly connected to drain 92. Drain pipe 124 includes a connector 126 that fluidly connects drain pipe 124 to bottom end 84 of level sensing tube 82.

When reservoir 38 is first coupled to thermal control unit 22, fluid flows out of reservoir 38 and into lower fluid chamber 110, as well as drain pipe 124. Further, if reservoir 38 contains the recommended amount of fluid, the fluid will travel through connector 126 and partially fill the bottom end 84 of level sensing tube 82. Because the upper end 80 of level sensing tube 82 is hermetically sealed and in gaseous communication with an air pressure sensor 78 contained within control box assembly 100, the air inside of level sensing tube 82 will be compressed by the partial filling of the bottom of level sensing tube 82. This will, in turn, cause the air contained therein to increase its pressure. As more fluid drains out of reservoir 38 and into thermal control unit 22, the level of fluid in the bottom end 84 of level sensing tube 82 will increase, further increasing the air pressure inside the top end 80 of level sensing tube 82. These pressure changes are detected by air pressure sensor 78, which is in electrical communication with controller 72. Controller 72 converts the air pressure changes into an indication of how much fluid is in control unit 22 and outputs this information on control panel 46.

Top end 80 of level sensing tube 82 includes a valve 130 that is adapted to automatically and hermetically seal the top end 80 of sensing tube 82 if it is ever disconnected from air pressure sensor 78. As was noted, air pressure sensor 78 is positioned inside of control box assembly 100 (on a circuit board contained therein), while the elements shown in FIGS. 10 and 11 (other than air pressure sensor 78) are mounted to the lower portion of frame 98 outside of control box assembly 100. In this manner, the amount of air contained within level sensing tube 82 above the fluid line (if present) will remain the same (although its volume will change due to increases or decreases in the total amount of fluid in unit 22).

As can be seen in greater detail in FIGS. 4, 10, and 11, thermal control unit 22 has its automatic drain plug 104 positioned adjacent to valve 70 and reservoir sensor 90. Automatic drain plug 104 is therefore pushed downward whenever reservoir 38 is coupled to thermal control unit 22. Due to the construction of automatic drain plug 104, which includes a movable internal plunger, the downward movement of the automatic drain plug will automatically close— to the extent it is open—drain 92. Thus, a user is automatically prevented from coupling reservoir 38 to thermal control unit 22 while drain 92 is open. This prevents the accidental draining of fluid out of reservoir 38 onto the floor, or other surface beneath control unit 22, when reservoir 38 is inserted into control unit 22.

Figure 12:
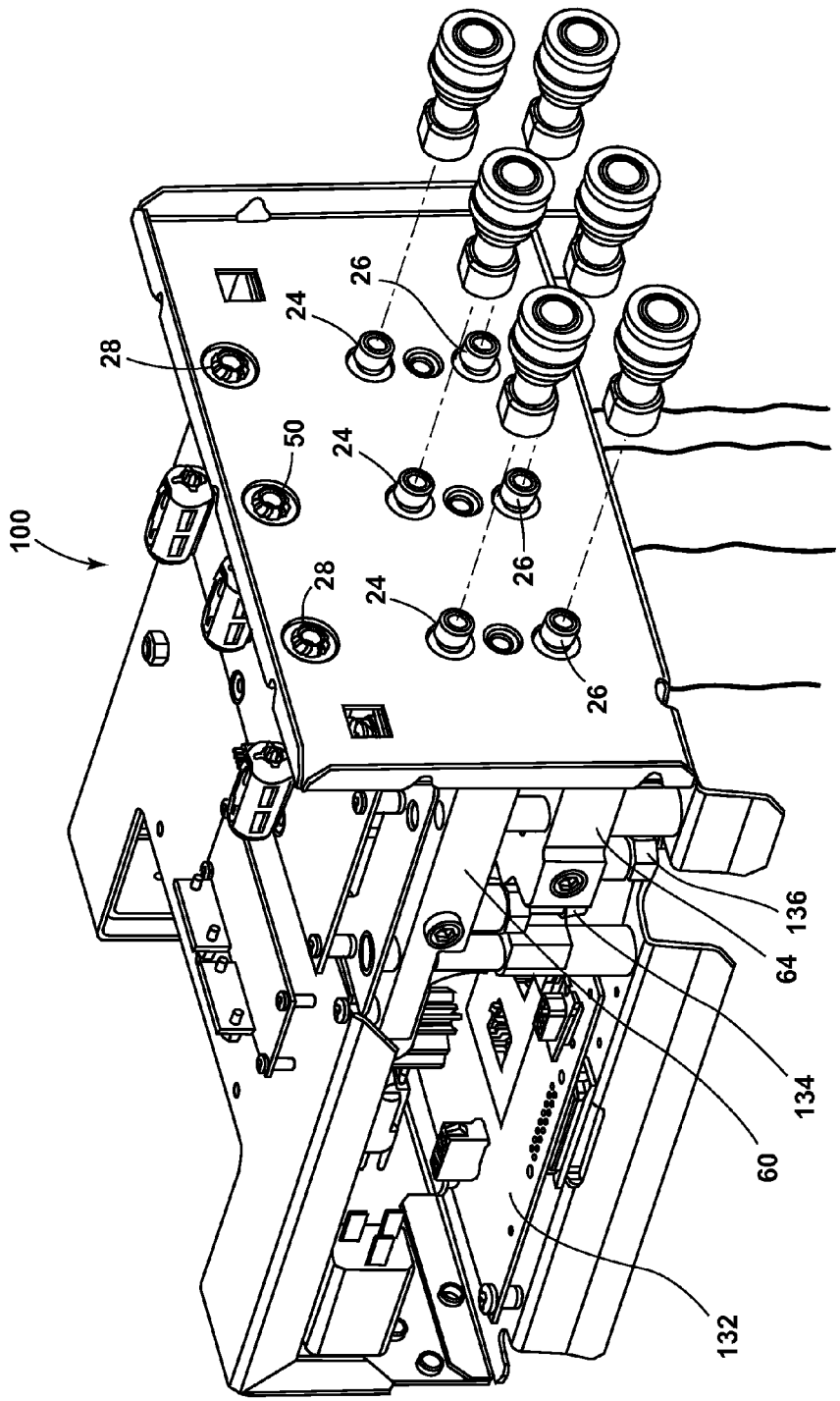
FIG. 12 is a perspective view of a control box of the thermal control unit of FIG. 2
Figure 13:
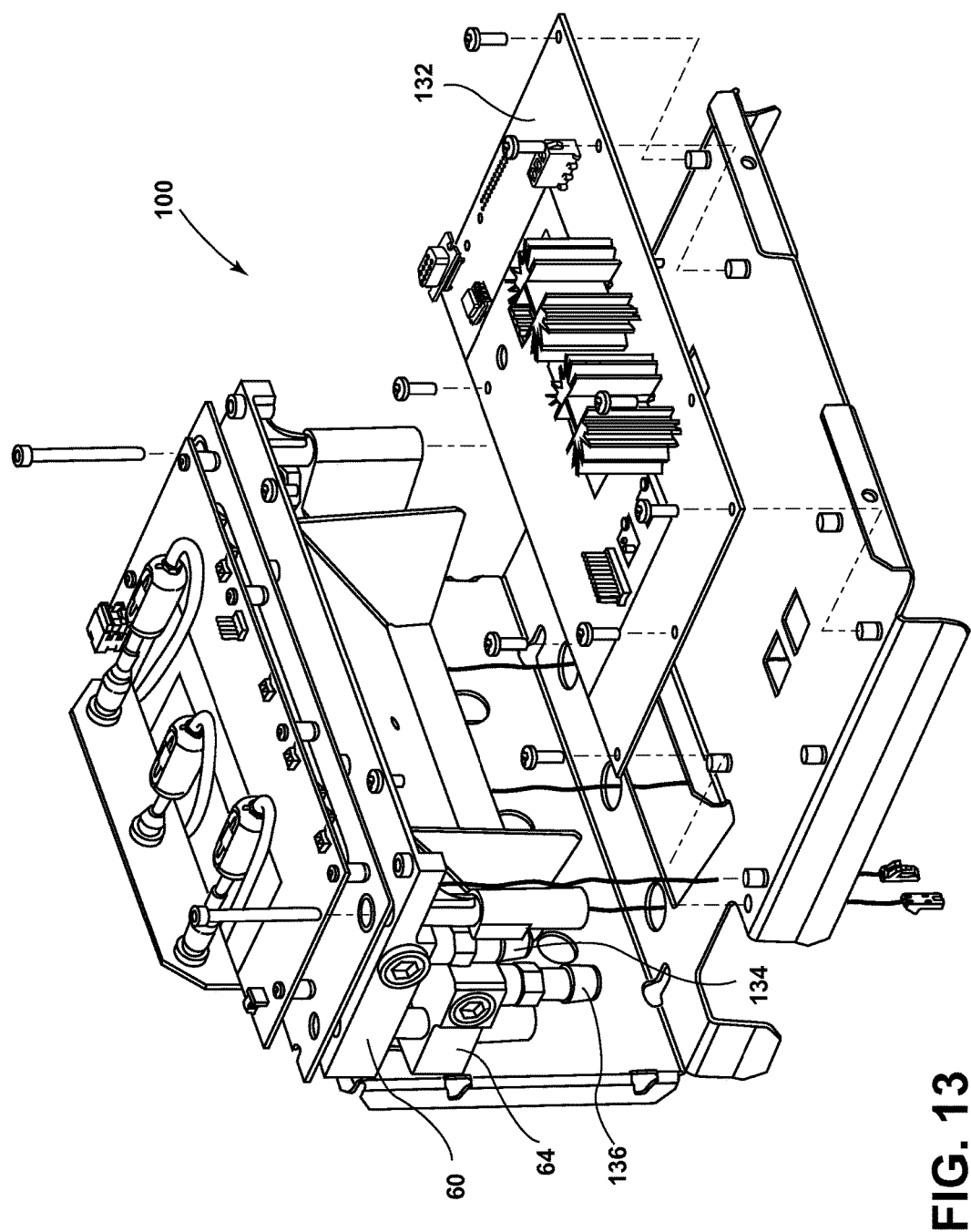
FIG. 13 is a partially exploded perspective view of the control box of FIG. 12 shown from an opposite side.
Figure 14:
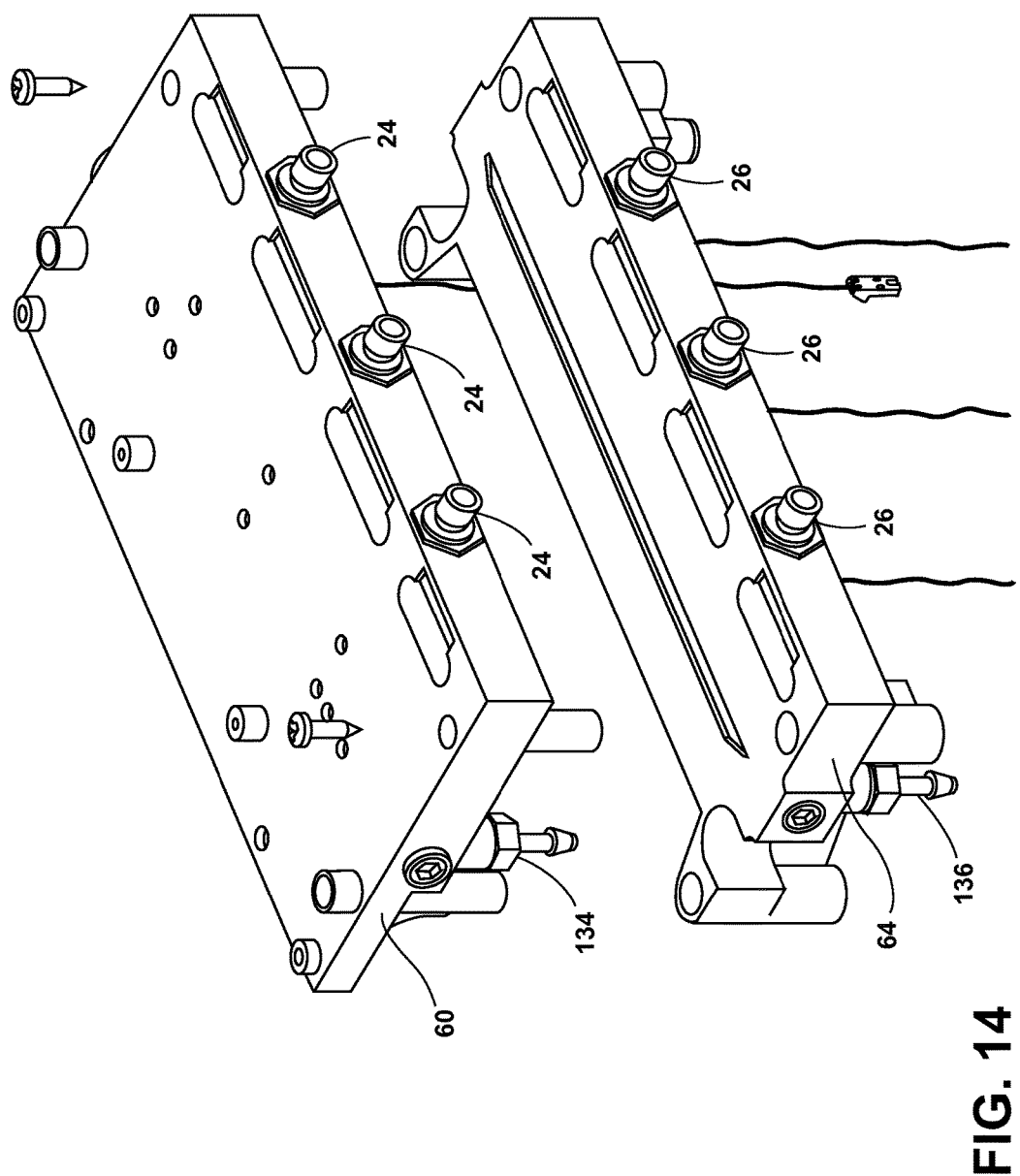
FIG. 14 is a perspective view of the inlet and outlet manifolds within the control box of FIG. 12.

FIGS. 12-14 illustrate in greater detail several aspects of control box assembly 100. Control box assembly 100 includes outlet manifold 60 and inlet manifold 64, as well as outlet ports 24 and inlet ports 26. Still further, control box assembly 100 includes patient temperature probe ports 28, patient temperature output port 50, and a circuit board 132 (FIG. 13) on which is mounted all, or some, of the components comprising controller 72. Bypass line 62 is not shown in FIGS. 12-14, but may include a hose connected between bypass ports defined on each of manifolds 60 and 64. If a filter 66 is included within the bypass line 62, the hose may first connect to the filter, and then connect to the inlet manifold 64. Fluid from pump 52 enters outlet manifold 60 through a supply port 134. Fluid exits inlet manifold 64 through an exit port 136, where the exiting fluid is delivered to pump inlet tube 106.

Figure 15:
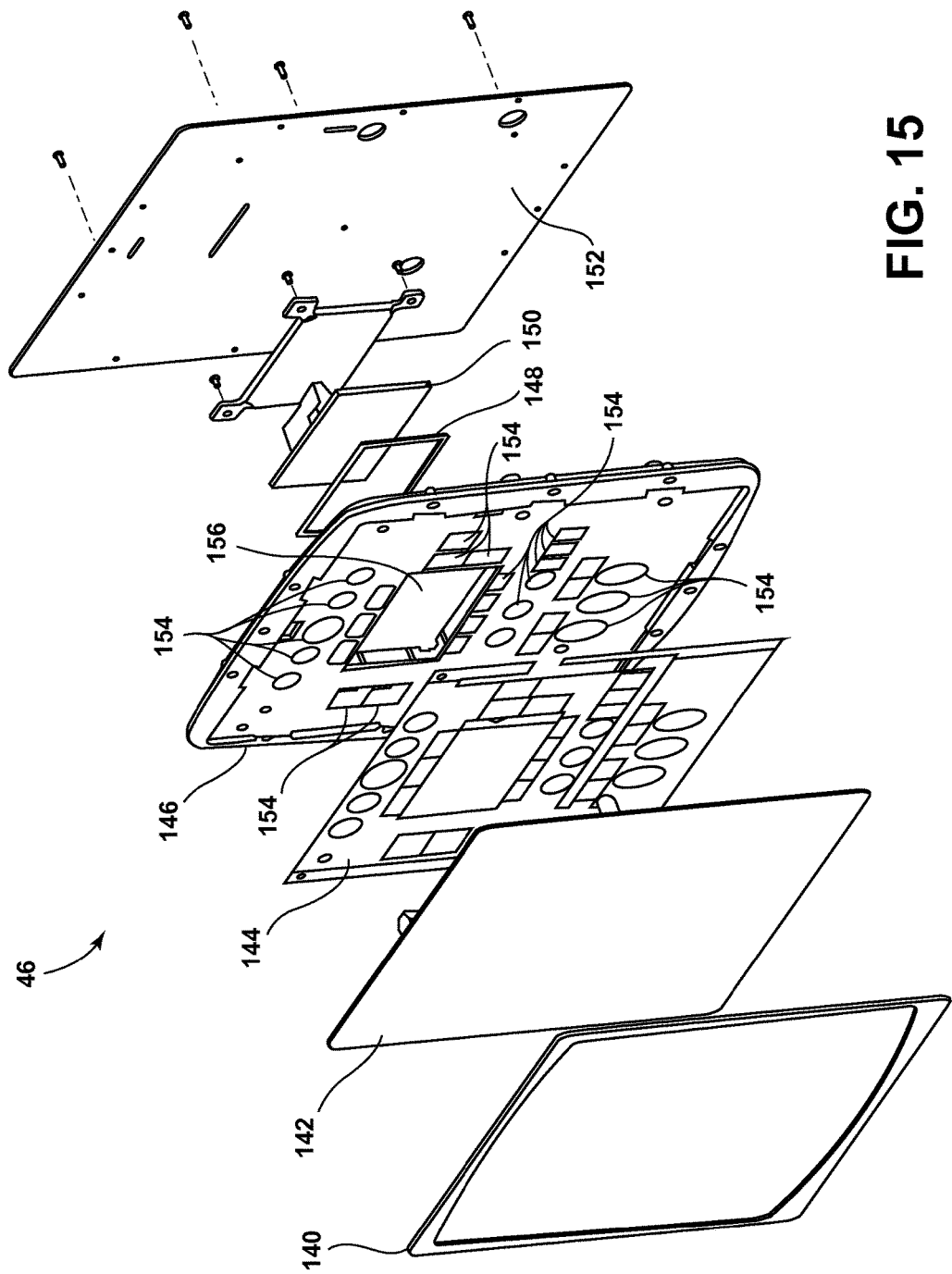
FIG. 15 is an exploded perspective view of the control panel of the thermal control unit of FIG. 2.

FIG. 15 illustrates in greater detail the construction of one configuration of control panel 46. As shown therein, control panel 46 includes a gasket 140, a generally planar sheet of glass 142, an indium tin oxide, or ITO, layer 144, a support bracket 146, an LCD gasket 148, an LCD (liquid crystal display) panel 150, and a circuit board 152. As can be seen in FIG. 15, support bracket 146 includes a plurality of fixed icon apertures 154 defined at locations where fixed icons are to be selectively displayed to the user of thermal control unit 22. The display of these fixed icons is selectively controlled by the electronics contained on circuit board 152, which includes a plurality of lights, such as Light Emitting Diodes (LEDs) positioned behind each of the fixed icon apertures 154. Controller 72, which communicates with circuit board 152, determines when to illuminate these LEDs, and thereby when to cause the fixed icon (which is defined on a side of glass layer 142 facing away from the user) corresponding to the fixed icon aperture 154 to appear. Further, for at least some of the icons, multiple LEDs that emit different colors are positioned behind the fixed icon apertures 154 on circuit board 152 so that the color of the icon can also be selectively controlled by circuit board 152 under the control of controller 72.

Support bracket 146 further includes an LCD aperture 156 defined at a location that aligns with LCD panel 150 so that the information displayed on LCD panel 150 may be seen through bracket 146. Unlike the fixed icon apertures 154, the LCD aperture 156 allows changing content to be viewed by the user of thermal control unit 22 because the LCD panel 150 is capable of displaying different graphics and images. In one embodiment, LCD panel 150 is a color LCD panel.

The ITO layer acts in a conventional manner to create a large area capacitive touchscreen over both the LCD panel 150 and each of the icons that align with each of the fixed icon apertures 154. When a user touches any of the icons, or any of the specific areas positioned over the LCD panel 150, controller 72 (which includes and/or oversees circuit board 152) will react accordingly.

Control panel 46 is designed so that whenever circuit board 152 does not illuminate an LED positioned behind a particular icon, that particular icon is substantially invisible to a user. This invisibility is created not only by the lack of any illumination from an LED positioned behind the icon, but also due to the fact that substantially no ambient light is permitted to enter and reflect from the area underneath glass layer 142. Such reflected light could otherwise provide some backlighting to the icons, rendering them visible. The area behind the icons, however, is black so that any such ambient light is substantially absorbed. Only when an adjacent LED is illuminated is light provided that passes through the icon on glass layer 142 and provides visibility of the icon to the user. In the absence of this light, the area where the icon is positioned is seen as a uniform background, such as a black background, by the user.

Figure 17:
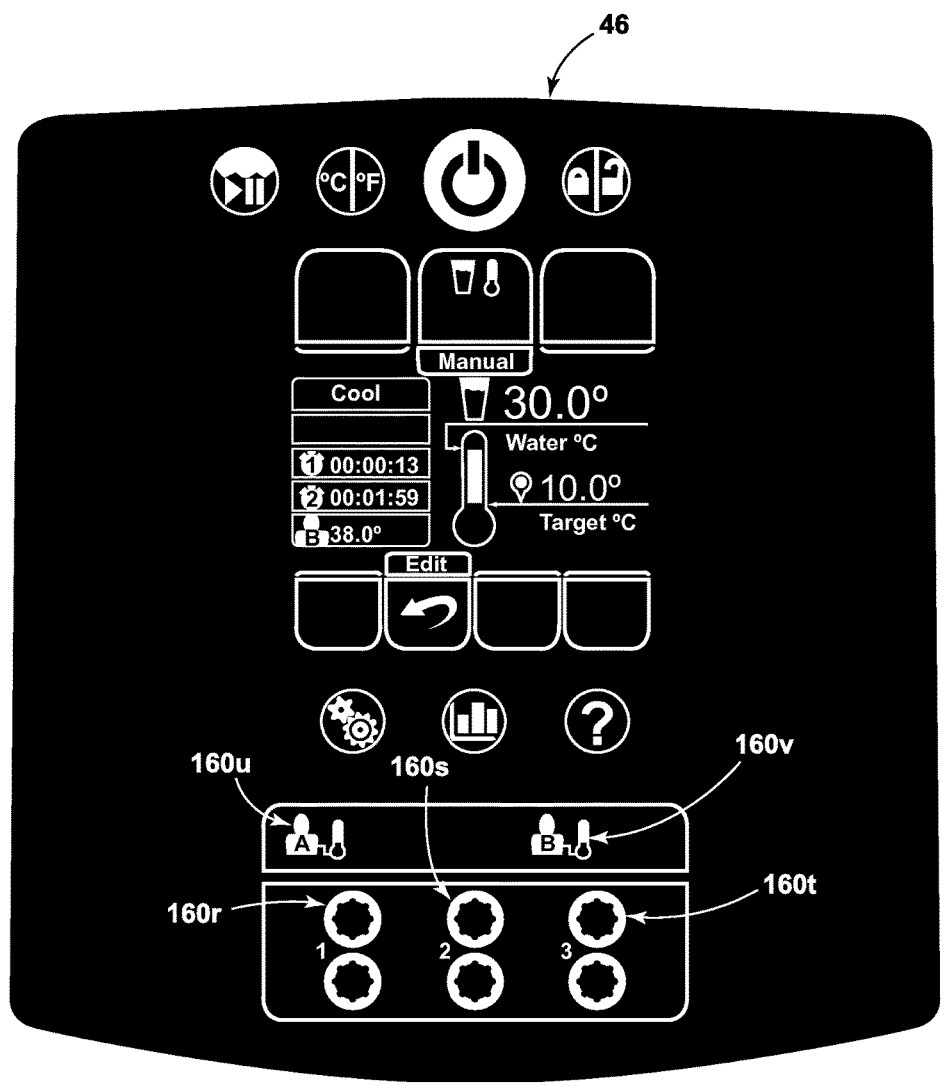
FIG. 17 is a first illustrative screen shot of the control panel illustrating the connection of three fluid lines to the thermal control unit.
Figure 18:
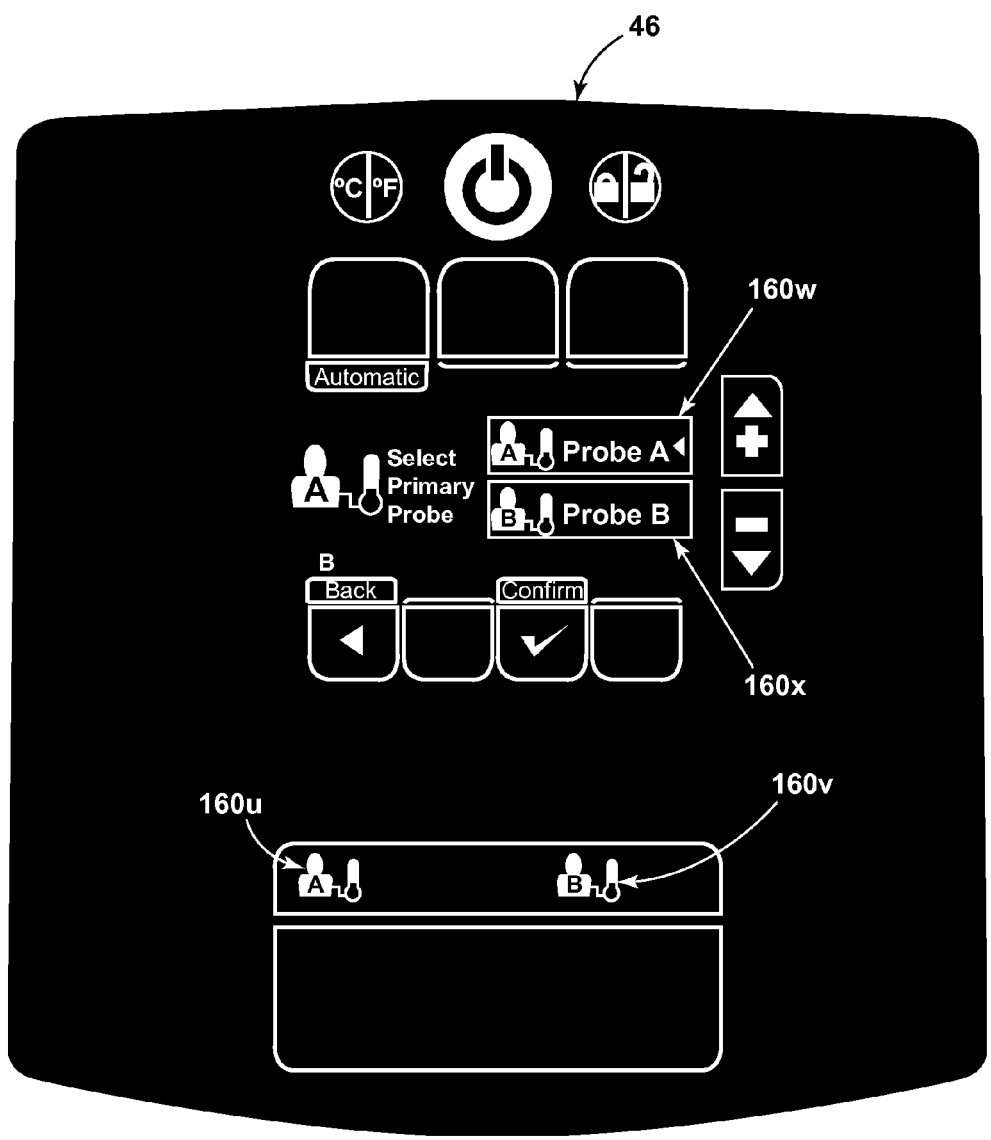
FIG. 18 is a second illustrative screen shot of the control panel illustrating one manner for a user to select a primary patient temperature probe.

One example of this selective visibility of icons is shown by a comparison of FIGS. 17 and 18. In FIG. 17, LEDs are illuminated behind icons 160$r$, 160$s$, 160$t$, 160$u$, and 160$v$ (whose functions are discussed below), thereby making these icons visible to a user. In FIG. 18, in contrast, the LEDs positioned behind icons 160$r$, 160$s$, and 160$t$ are not illuminated, and the area where icons 160$r$, 160$s$, and 160$t$ would otherwise appear on control panel 46 appears black to a user. This selective visibility gives control panel 46 the ability to change the graphical information displayed to a user not only in the area of LCD panel 150, but also in the areas outside of LCD panel 150. Further, this selective visibility allows for the decluttering of icons on control panel 46 at times when the display of one or more icons is not necessary. It also provides an indication to a user as to what control options are currently available and/or what information is currently relevant, thereby assisting the user as to what actions he or she can take at any given moment (e.g. by pressing one or more icons 160). Controller 72 therefore selectively renders icons 160 visible and invisible according to the current state of control unit 22, thereby selectively providing the user with information and/or control options that are tailored to the current state of the control unit 22.

Figure 16:
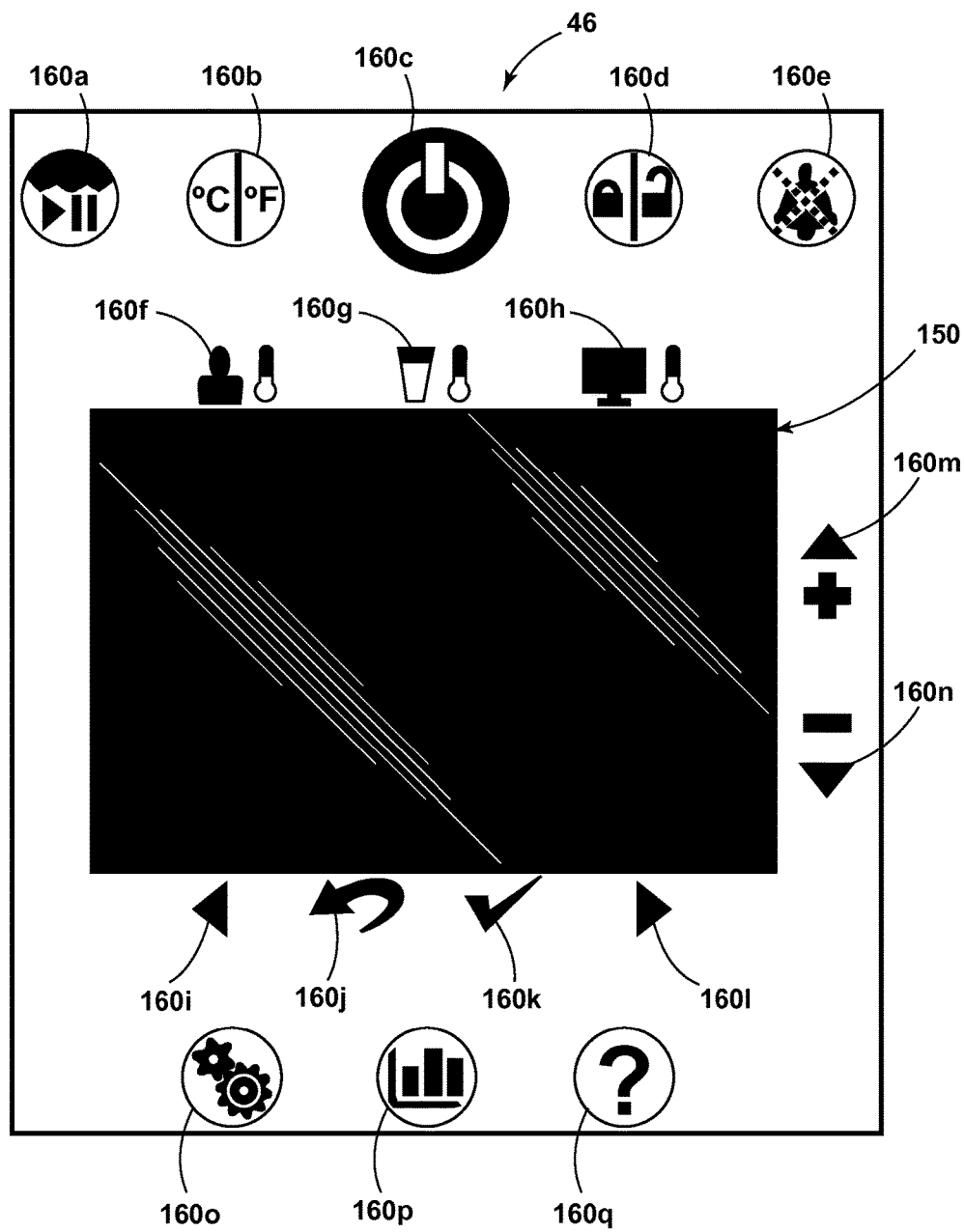
FIG. 16 is a plan view of the touch screen surface of the control panel showing an LCD area and a fixed icon area.
Figure 19:
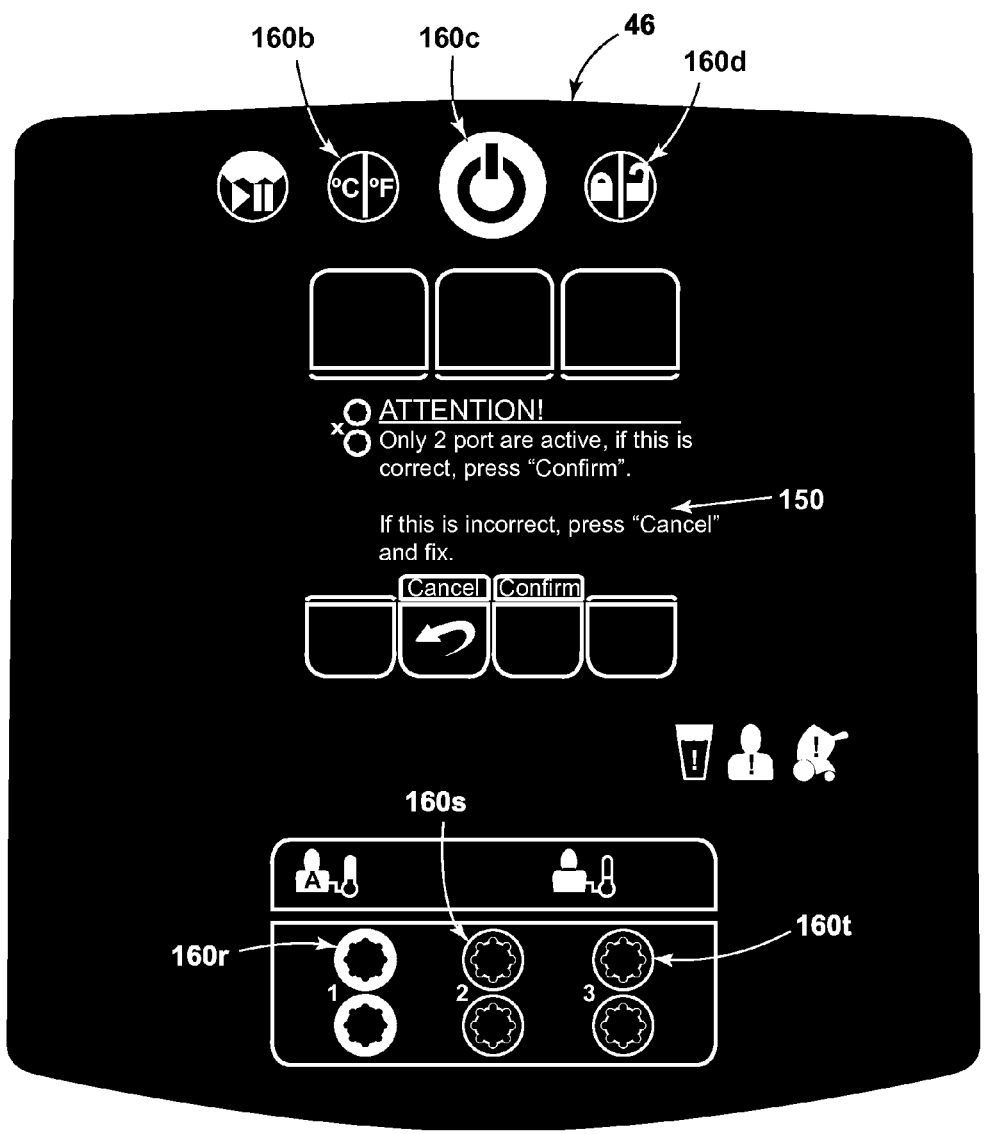
FIG. 19 is a third illustrative screen shot of the control panel illustrating one manner for allowing a user to designate active and inactive flow ports.

FIG. 16 shows one manner in which the layout of control panel 46 can be implemented, including an illustrative arrangement of fixed icons that are selectively displayable on control panel 46. As can be seen, control panel 46 includes a plurality of fixed icons 160 that are positioned around LCD screen 150. The manner in which these icons 160 are shown in FIG. 16 is not representative of the manner in which these icons are actually seen by a user. That is, FIG. 16 illustrates icons 160 as being dark images printed on a white background. This is merely for purposes of illustrating the position and shape of icons 160. The manner in which a user actually views these icons 160 is shown in FIGS. 17-19 where the icons 160 are selectively displayed against a black background and are otherwise invisible if not illuminated, as was discussed in greater detail above. Control panel 46, in one embodiment, therefore presents illuminated graphics to a user that are displayed against a black background.

Icons 160 include a therapy pause icon 160a that, when pressed, pauses the therapy being performed by thermal control unit 22 (FIG. 16). To resume therapy, a user presses and holds down on the therapy pause icon 160a. A selection icon 160b allows a user to switch between displaying the temperatures in Fahrenheit and Celsius by pressing on icon 160b, which acts as a toggle switch between the two different units of measurement. A power icon 160c will turn on and off thermal control unit 22 when pressed. When a user first presses a lock icon 160d, the screen will be locked and pressing on any areas of the screen will not change any settings, or otherwise cause thermal control unit 22 to react to the pressing. In order to unlock the touchscreen, a user presses down and holds the lock icon 160d for at least two seconds. An audio pause icon 160e, when pressed, silences any audible alarms for a predetermined period of time, such as ten minutes. Any alarms will still result in a visual display of the alarm on control panel 46, but will not result in any audible indications while the audio pause is in effect.

Control panel 46 further includes three therapy mode icons 160f, 160g, and 160h. Pushing down on mode icon 160f will cause thermal control unit 22 to act in the automatic mode (described previously). Pushing down on mode icon 160g will cause thermal control unit 22 to act in the manual mode (also described previously). Pushing down on mode icon 160h will cause thermal control unit 22 to act in a monitor mode (not described previously). In the monitor mode, thermal control unit 22 does not circulate fluid or regulate the fluid's temperature, but instead merely monitors the temperature(s) input into thermal control unit 22 via the patient temperature probe ports 28 and issues any alarms if the temperatures change beyond any user-defined thresholds.

A back icon 160i causes controller 72 to change what is displayed on LCD screen 150 to that which was displayed thereon immediately prior to the pressing of the back icon 160i. An edit icon 160j will enable the user to edit current settings when pressed, or exit or cancel, depending upon the context of the information displayed on LCD screen 150. A confirm icon 160k, when pressed, allows a user to confirm a selection made by the user of information displayed on LCD screen 150. A forward icon 160l will shift, when pressed, what is displayed on LCD screen 150 to the next sequential screen.

Icon 160o is a settings icon that, when pressed, displays a summary of the current settings of thermal control unit 22. Pressing on graphic icon 160p will graphically display the measured and recorded patient temperatures, the target temperature, the fluid temperature and working capacity. A help icon 160q displays contextual help screens for therapies, navigation, and button usage.

Finally, icons 160m and 160n enable a user to increase or decrease a patient or fluid temperature, depending upon the context of what is displayed on LCD screen 150.

Although not illustrated in FIG. 16, control panel 46 further includes several additional fixed icons, several of which are displayed in FIGS. 17 and 18. For example, in FIG. 17, control panel 46 is shown displaying a port 1 icon 160r, a port 2 icon 160s, and a port 3 icon 160t. These icons 160r, s, and t are displayed when thermal control unit 22 detects that a hose has been coupled to one or more of the three outlet ports 24. The coupling of a hose to one or more of the three outlet ports 24 is detected by way of pressure sensors 76b, c, and d (or turbine flow sensors, if used), which together form a sensing subsystem for detecting the presence and absence of supply and returns lines 30a and 30b. That is, controller 72 monitors the outputs of pressure sensors 76b, c, and d (or turbine flow sensors, if used) to compute individual flow rates for each outlet port 24. If no flow rate is detected for a particular port, then controller 72 does not illuminate the corresponding port icon 160r, s, or t. If a flow rate is detected that is within a normal range for a particular port, then controller 72 illuminates the corresponding port icon 160r, s, or t with a green color. If flow is detected by controller 72 for a particular outlet port 24, but the flow rate is beneath a threshold that likely indicates a constricted flow, or other undesirable situation, then controller 72 displays the corresponding port icon 160r, s, or t in a yellow color. In one embodiment, the threshold is set to a flow rate less than a half of a liter per minute. Control panel 46 thereby provides visual feedback and indications to the user of which ports are in proper working order. This individual monitoring of the flow through each port helps ensure that no thermal pad has its fluid flow partially obstructed, which might otherwise be difficult to detect in a manual and visual manner by a user. The sensing subsystem for detecting this fluid flow may take on different forms from the pressure sensors 76b, c, and d mentioned above, such as, but not limited to, direct flow measurements sensors, or other types of sensors.

FIG. 17 also illustrates icons 160u and 160v on control panel 46. Icon 160u, which may be illuminated in a green color, indicates that a first patient temperature probe 34 is connected to a patient temperature probe port 28 and the patient temperature probe 34 is active. Icon 160v indicates the same information for a second patient temperature probe 34 that may be connected to the second patient temperature probe port 28.

FIG. 18 shows an illustrative screen that may be displayed on LCD screen 150 of control panel 46 for enabling a user to select which of the multiple patient temperature probes 34 is to be the primary patient temperature probe (i.e. the one which provides temperature outputs that the thermal control unit 22 is trying to control). By pressing on icon 160w, the user is able to select patient temperature probe A as the primary patient temperature probe. Alternatively, the user is able to select patient temperature probe B as the primary patient temperature probe 34 by pressing on icon 160x. Probes A and B are coupled to each of the two patient temperature probe ports 28 on control unit 22. As was noted previously, the selection of probe A or B as the primary probe also determines what temperature control unit 22 will output at patient temperature output port 50. In other words, the probe that has been selected as the primary probe will have its temperature readings both forwarded to patient temperature output port 50 and used by controller 72 to control the temperature of the circulating fluid (when unit 22 is operating in the automatic mode).

In an alternative embodiment, control panel 46 is modified to display a screen similar to that of FIG. 18 but modified to allow the user to select more than one temperature probe 34 as the primary temperature probe. This modified screen may further include one or more additional control messages, indicia, information, and/or selections that allow the user to select the manner in which control unit 22 uses the readings from the multiple temperature probes 34. As was noted previously, the manner of using the temperature readings from probes 34 may include, but is not limited to, various mathematical combinations (averages, weighted averages, etc.) of the temperatures from probes 34.

FIG. 19 shows an illustrative configuration of control panel 46 that is adapted to allow a user to select which of ports 24 and 26 are to be considered "active" and which are to be considered "inactive." Controller 72 monitors the outputs of the flow sensors 76*b*, *c*, and *d* (which form a sensing subsystem) to determine whether any fluid is flowing through ports 24. For those ports in which fluid flow is detected, controller 72 makes a preliminary determination that those ports are intended by the user to be active. For those ports in which no fluid flow is detected, controller 72 makes a preliminary determination that those ports are intended by the user to be inactive. Controller 72 then causes control panel 46 to display the configuration shown in FIG. 19, which requests that the user confirm or cancel the preliminary determination of active and inactive ports made by controller 72. In the example shown in FIG. 19, controller 72 has detected flow in outlet ports 2 and 3, and detected no flow in outlet port 1. Controller 72 therefore illuminates icons 160*s* and 160*t* (corresponding to outlet ports 2 and 3) in a first color (such as, but not limited to, green) and illuminates icon 160*r* (corresponding to outlet port 1) in a second color (such as, but not limited to, yellow). Controller 72 further causes LCD panel 150 to display a question or prompt to the user asking that he or she confirm or disconfirm that ports 2 and 3 are to be the active ports and port 1 is to be inactive. The user confirms or disconfirms this by pressing the "confirm" button or "cancel" button, respectively, as shown in FIG. 16.

When a user confirms that one or more outlet ports 24 are to be considered inactive, controller 72 ceases to display the corresponding icon for that particular port. Thus, for example, in the configuration shown in FIG. 19, if a user were to press the confirm button to confirm that port 1 was to be inactive, controller 72 would thereafter cease to illuminate icon 160*r*, rendering it invisible to the user. Icons 160*s* and 160*t*, however, which correspond to the active ports, would continue to be illuminated and controller 72 would change the color of this illumination based upon the current state of these ports. For example, as mentioned previously, if the fluid flow for either of these ports were to drop below a threshold, controller 72 will change the display of the corresponding icon 160*s* or 160*t* from green to yellow, or to some other color to indicate that a potentially undesirable condition exists for that fluid port.

Once a user has designated which ports are active and which, if any, are inactive, controller 72 will provide temperature data for those inlet ports 26 that are active, as measured by temperature sensors 74*b*, *c*, and *d*. Controller 72 will further provide an indication to the user if the temperatures sensed by the sensors 74*b*, *c*, and/or *d* that are associated with active ports detect temperatures that are outside of an acceptable range. Still further, controller 72 will provide an indication to the user any time any changes are detected that indicate a potential change in which ports are to be active and which ports are to be inactive. In other words, if any supply or return lines 30*a* or 30*b* are disconnected from a set of active ports 24, 26, or if any supply or return lines 30*a* or 30*b* are connected to a set of inactive ports 24, 26, controller 72 will sense these changes, via pressure sensors 76, *b*, *c*, and/or *d*, (or turbine flow sensors, if used) and will present information on control panel 72 alerting a user of these changes. The alert will further request confirmation from the user that the detected connection or disconnection was intended.

Figure 20:
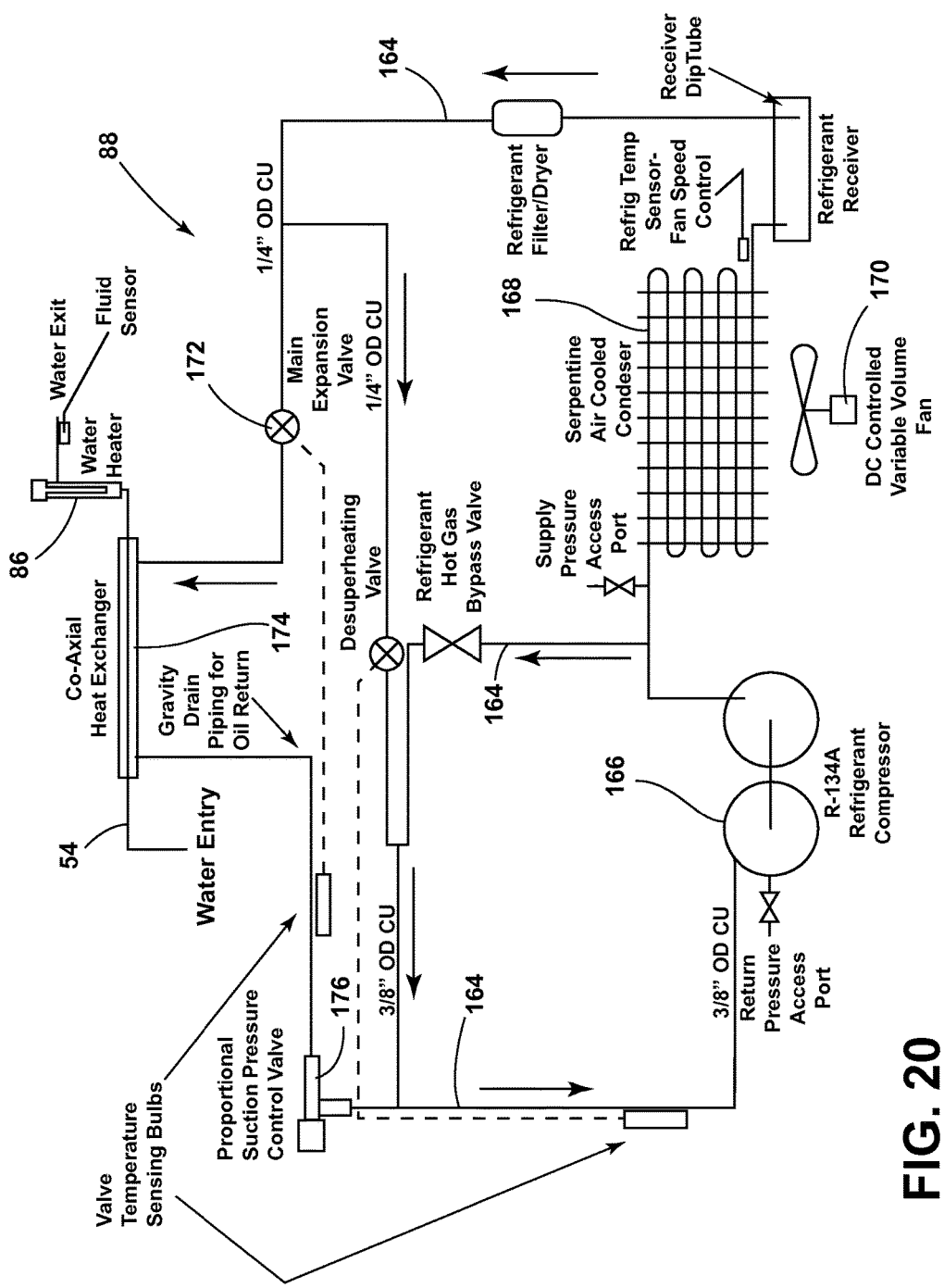
FIG. 20 is a diagram of a refrigeration unit within the thermal control unit of FIG. 2.

FIG. 20 illustrates a diagram of the internal layout of the chiller 88, including a refrigerant flow path 164. Chiller 88 includes a compressor 166, a condenser 168 that is selectively cooled by a DC controlled fan 170, an expansion valve 172, a co-axial heat exchanger 174, and a pressure control valve 176. The co-axial heat exchanger 174 is in thermal communication with the fluid flowing through circulation channel 54. That is, the fluid flowing through circulation channel 54 has its temperature selectively cooled during its passage through coaxial heat exchanger 174. During the flow of fluid through coaxial heat exchanger 174, the fluid maintains its physical separation from the refrigerant contained within, and flowing through, flow path 164.

Controller 72 oversees the operation of chiller 88. In order to more accurately control the temperature of the refrigerant supplied to coaxial heat exchanger 174, controller 72 controls the amount of refrigerant flowing through condenser 168 by selectively opening and closing pressure control valve 176. Because pressure control valve 176 is located downstream of condenser of the coaxial heat exchanger 174, more precise and fine control of the amount of refrigerant evaporated in heat exchanger 174 is accomplished, thereby giving controller 72 a finer ability to precisely control the temperature of the refrigerant in heat exchanger 174. This finer and/or more precise temperature control means that the fluid flowing through heat exchanger 174 within channel 54 can have its temperature more precisely controlled, thereby reducing potential problems with overshoot while still eliminating the need of a tank.

In some other embodiments, chiller 88 is further in communication with an ambient air sensor. The ambient air sensor detects the temperature of the ambient air in the vicinity of control unit 22. Controller 72 uses this ambient air temperature in determining how fast to operate fan 170. This allows controller 72 to more precisely control the refrigerant temperature, which also allows control unit 22 to more precisely control the fluid temperature.

Figure 21:
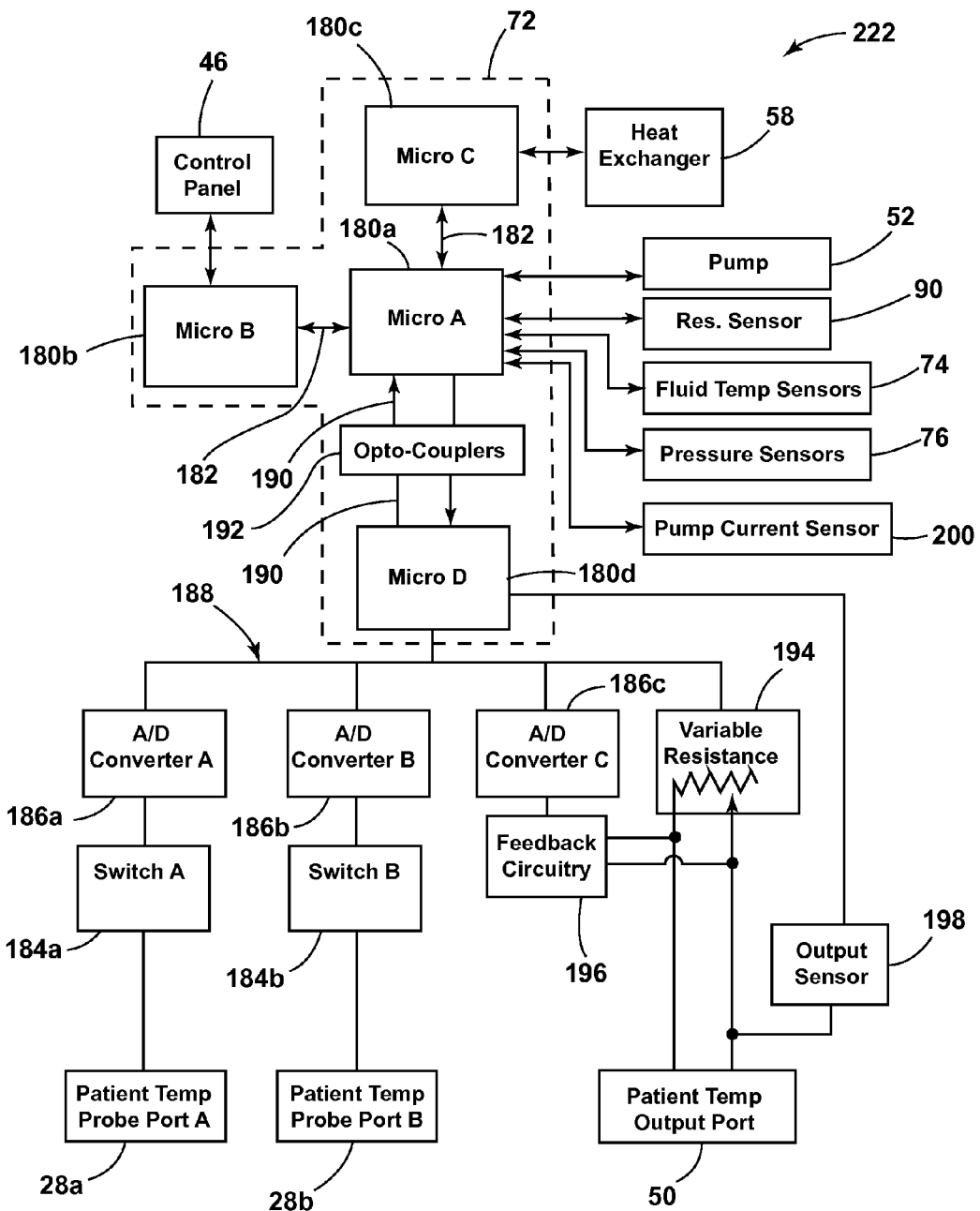
FIG. 21 is a block diagram of an alternative embodiment of the thermal control system.

FIG. 21 shows a schematic diagram of the major components of another embodiment of control unit 222. Those components of control unit 222 that are in common with control unit 22 and that operate in the same manner as control unit 22 are labeled with the same reference numbers. Control unit 222 includes a controller 72 that comprises four separate microcontrollers 180*a*, *b*, *c*, and *d*. In this embodiment, microcontrollers 180*a*, *b*, *c*, and *d* are commercially available off-the-shelf conventional microcontrollers. Microcontrollers 180*a*, *b*, and *c* are in communication with each other via a Controller Area Network (CAN) bus 182 that operates in accordance with the International Organization for Standardization (ISO) 11898 standard. This standard defines the physical and data link layers (levels 1 and 2 of the ISO/OSI model). Additional higher level layers that use the CAN physical and data link layers may be used with microcontrollers 180*a*, *b*, and/or *c*, such as, but not limited to CANOpen. The CAN bus 182, which these microcontrollers 180*a, b*, and *c* use to communicate with each other, can utilize either the standard frame format (CAN 2.0A), which utilizes 11 bit identifiers in the message frames, or the extended frame format (CAN 2.0B), which utilizes 29 bit identifiers in the message frames.

Microcontroller 180*a* is the main microcontroller that oversees the operation of control unit 22. Microcontroller 180*b* oversees and manages the control panel 46, communicating the user inputs to main microcontroller 180*a* as needed, and receiving information from main microcontroller 180*a* for display on control panel 46. Microcontroller 180*c* oversees the heat exchanger 58 which, in this embodiment, includes both heater 86 and chiller 88. Microcontroller 180*d* reads the temperature information that is input from either or both of patient temperature probe ports 28*a* and *b* and communicates this temperature information to main microcontroller 180*a*. Microcontroller 180*d* also controls the information that is output at patient temperature output port 50.

More specifically, microcontroller 180*d* determines the current amount of electrical resistance at each patient temperature probe port 28*a* and 28*b* (which corresponds to the current temperature being sensed by each of the patient temperature probes 34 that are inserted into these ports 28*a, b*). Microcontroller 180*d* reads the resistance at port A by closing a first switch 184*a* while opening a second switch 184*b*. The resistance sensed at port A is converted to a digital value by a first Analog-to-Digital (ND) converter 186*a*, which forwards the digital value to microcontroller 180*d* over a serial peripheral interface (SPI) bus 188. In order to read the electrical resistance at patient temperature probe port 28*b*, microcontroller 180*d* closes switch 184*b*, opens switch 184*a*, and receives the digital resistance value from a second ND converter 186*b* over SPI bus 188.

After reading the electrical resistances as ports 28*a* and 28*b*, microcontroller 180*d* converts these electrical resistances to temperature values using the known relationship between the probe resistances and temperature. Microcontroller 180*d* then forwards these temperature readings to main microcontroller 180*a* over a serial line 190 that passes through one or more opto-couplers 192. Opto-couplers 192 provide electrical isolation between microcontroller 180*d* and main microcontroller 180*a*. Main microcontroller 180*a* forwards these temperature readings to microcontroller 180*b* for display on control panel 46. Further, main microcontroller 180*a* forwards at least that one of these two temperature readings to microcontroller 180*c* that corresponds to the port 28*a* or 28*b* that has been designated by the user as being the primary port. Microcontroller 180*c* uses the patient temperatures readings from the primary port (28*a* or 28*b*) to control the temperature of the circulating fluid when the control unit 222 is operating in the automatic mode.

Microcontroller 180*d* also controls and changes the electrical resistance of a variable resistance device 194 so that it will have the same, or nearly the same, electrical resistance as the resistance that microcontroller 180*d* is currently measuring from whichever one of ports 28*a* and 28*b* the user has designated as the primary port. In other words, microcontroller 180*d* re-creates with device 194 the electrical resistance that it is currently reading at port 28*a* or 28*b* (whichever is the primary port). A separate medical device or monitor can therefore insert a patient temperature probe into patient temperature output port 50, read the resistance of variable resistance device 194, and determine the temperature of the patient that is being sensed by the primary patient temperature probe 34.

In order to accurately generate the desired electrical resistance in variable resistance device 194, microcontroller 180*d* utilizes feedback circuitry 196. Feedback circuitry 196 measures the electrical resistance of variable resistance device 194 and sends it to an ND converter 186*c*, which forwards the corresponding digitized value of the resistance measurement to microcontroller 180*d*. Microcontroller 180*d* compares this measured resistance to the resistance it is attempting to generate in device 194 (the target resistance). To the extent there is any difference, microcontroller 180*d* makes necessary adjustments so that the actual resistance of device 194 will be substantially equal to the target resistance. In this manner, microcontroller 180*d* uses closed-loop feedback to generate a precise resistance value at device 194.

In one embodiment, feedback circuitry 196 reads the actual resistance of variable resistance device 194 by applying a constant current to device 194 and measuring the corresponding voltage drop across device 194. This voltage drop will be directly proportional to the value of the resistance. Microcontroller 180*d* converts the voltage reading to a resistance value. In order to avoid interference between the resistance measurements made by feedback circuitry 196 and measurements made by an external probe (connected to port 50), control unit 222 includes an output sensor 198 that detects whether a probe is connected to port 50 or not. When a probe is connected, that probe will supply its own constant current to variable resistance device 194 in order to measure the electrical resistance of device 194. Therefore, in order to avoid having both the probe and feedback circuitry 196 simultaneously applying a constant current to variable resistance device 194, microcontroller 180*d* will automatically shut off the constant current source within feedback circuitry 196 whenever a probe is coupled to port 50, as detected by sensor 198. In those situations, feedback circuitry 196 will utilize the constant current supplied through port 50 to measure the resistance of variable resistance device 194. When a probe is not connected to port 50, however, sensor 198 will sense this fact, communicate it to microcontroller 180*d*, and microcontroller 180*d* will instruct feedback circuitry 196 to turn on its own internal constant current source to enable it to measure the actual resistance of device 194.

Control unit 222 further includes a pump current sensor 200 that is adapted to measure the amount of electrical current that is being consumed by pump 52 when it is activated. Microcontroller 180*a* uses this measurement to determine whether or not sufficient fluid is present in system 20. Microcontroller 180*a* makes this determination by comparing the amount of electrical current being consumed by pump 52 to a pre-stored value that has been experimentally derived from prior usage of control unit 222. That is, the pre-stored value is determined by taking readings of the electrical current usage of pump 52 when different amounts of fluid are present within system 20, including situations in which an insufficient amount of fluid is present. In those situations where insufficient fluid is present, the current used by pump 52 will be measurably less than those situations in which a sufficient fluid supply is present. Microcontroller 180*a* therefore determines whether or not sufficient fluid is present by monitoring the output of sensor 200 and comparing it with the pre-stored value, which is stored in a memory (not labeled) accessible to microcontroller 180*a*.

Microcontroller 180*a*, in one embodiment, analyzes the output of current sensor 200 in conjunction with the outputs of other sensors before determining whether pump 52 should be shut down or not. For example, in one embodiment, microcontroller 180*a* also analyzes the output from flow sensors 76*b, c, d,* and *e* (whether implemented as pressure sensors or turbine flow sensors). Microcontroller 180*a* will automatically shut down pump 52 if current sensor 200 indicates that insufficient flow is present and if none of sensors 76*b, c, d,* and *e* are detecting flow rates that are indicative of sufficient fluid volume. If, however, current sensor 200 indicates that insufficient flow is present, but one or more of sensors 76*b, c, d,* or *e* indicate sufficient fluid flow, controller 72 will flag this condition to the user as a possible error, but will continue to power pump 52 and provide therapy to a patient.

In still other embodiments, control unit 22 may also include a fluid level sensor, such as the air pressure sensor 78 discussed above, or a fluid level sensor 202, which is discussed in more detail below, in addition to current sensor 200. By using both a fluid level sensor and a current level sensor 200 (and also sensors 76*b, c, d,* and/or *e*, if desired, whether implemented as pressure sensors or turbine sensors) redundancy is provided for detecting fluid levels. This redundancy allows therapy to be continued to a patient if only one of the redundant sensors indicates insufficient fluid flow.

Figure 23:
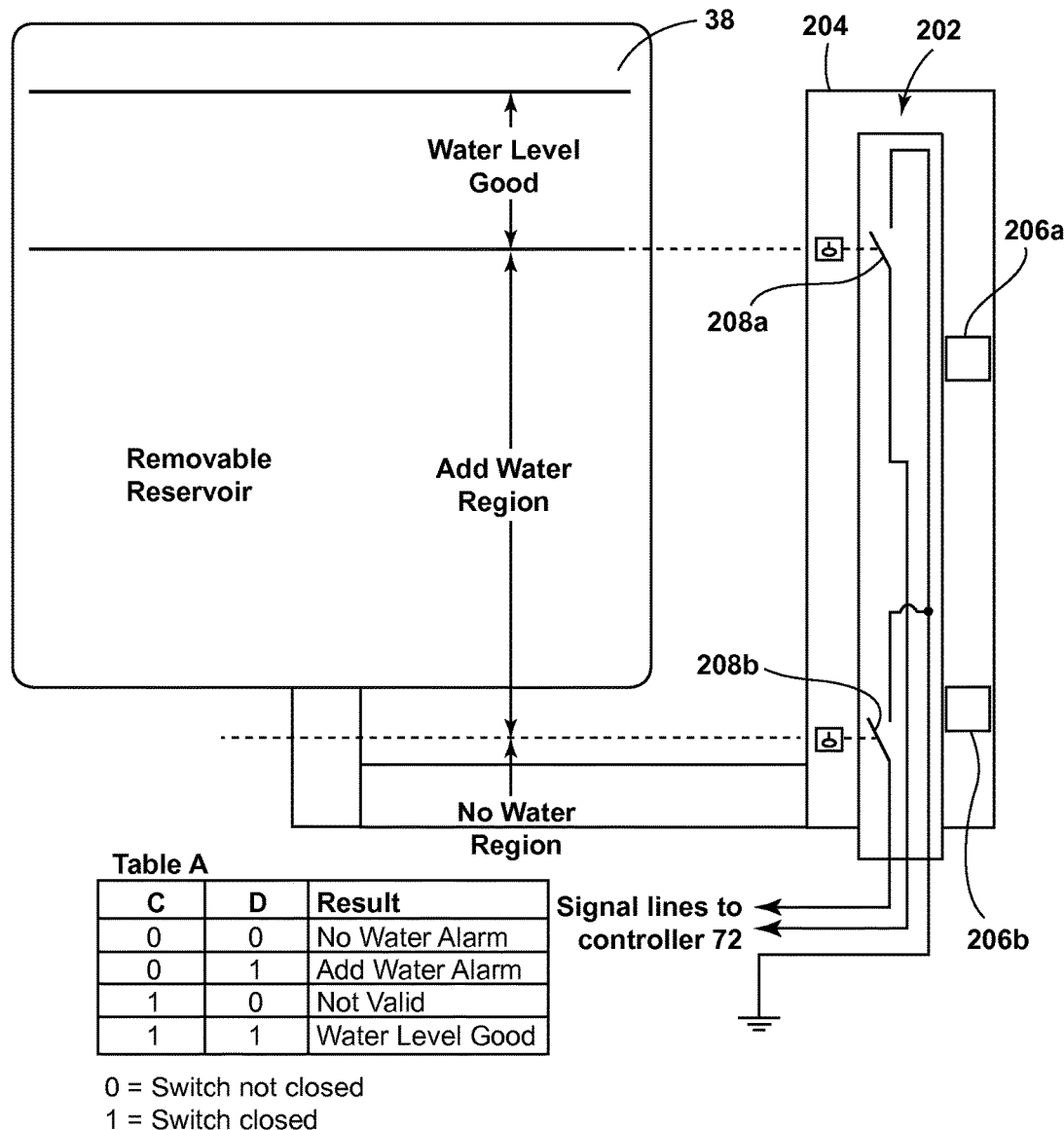
FIG. 23 is a diagram of an alternative fluid level sensor that may be used with any of the thermal control units disclosed herein.

FIG. 23 shows a block diagram of a fluid level sensor 202 that may be used in place of air pressure sensor 78 and level sensing tube 82, discussed above. Fluid level sensor 202 may also be used either in place of, or in combination with, the pump current sensor 200 discussed above. Fluid level sensor 202 is positioned inside of a vertical fluid level tube 204 that is in fluid communication with removable reservoir 38. This fluid communication ensures that the fluid in fluid level tube 204 will rise to the same height as the fluid inside of removable reservoir 38. In one embodiment, fluid level tube 204 is positioned in the same location as level sensing tube 82 but, unlike level sensing tube 82, it is vented to atmosphere at its top end rather than being in fluid communication with air pressure sensor 78.

An upper float 206*a* and a lower float 206*b* are positioned inside of fluid level sensing tube 82. Each of upper and lower floats 206*a* and 206*b* carry magnets. An upper Reed switch 208*a* and a lower Reed switch 208*b* are positioned either inside of tube 204, or adjacent the exterior of tube 204. When removable reservoir 38 is placed into fluid connection with control unit 22, the fluid will fill tube 204 to the same height as reservoir 38. As the fluid fills tube 204, the lower float 206*b* will rise with the rising fluid level until it reaches a position located adjacent lower Reed switch 208*b*, where it will be prevented from further upward movement by a mechanical stop (not shown). When lower float 206*b* reaches lower Reed switch 208*b*, the magnet on lower float 206*b* will close the lower Reed switch 208*b*, which will be sensed by controller 72. As the fluid level inside of tube 204 continues to rise further, it may eventually reach upper float 206*a*. If sufficient fluid is present, float 206*a* will be lifted up until it is positioned adjacent upper Reed switch 208*a*, at which point the magnet will close upper Reed switch 208*a*. The closing of upper Reed switch 208*a* will be sensed by controller 72. Controller 72 will therefore be presented with the outputs from Reed switches 208*a* and 208*b* and will know whether sufficient fluid is present, whether no fluid is present, or whether some fluid is present but more needs to be added. The logic for determining these three states if shown in Table A of FIG. 23.

More specifically, if both Reed switches 208*a* and *b* are open, then a "no fluid" alert is activated. If lower Reed switch 208*b* is closed, but upper Reed switch 208*a* is open, then enough fluid is present to float lower float 206*b* up to Reed switch 208*b*, but not enough to float upper float 206*a* up to upper Reed switch 208*a*. Thus, in this condition, controller 72 will issue an "add fluid" alert. Finally, if both Reed switches 208*a* and 208*b* are closed, then sufficient water is present and controller 72 does not issue any fluid level alert.

Various alterations and changes can be made to the above-described embodiments without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular.

What is claimed is:

1. A thermal control unit comprising:
   a first fluid outlet adapted to fluidly couple to a first fluid supply line;
   a second fluid outlet adapted to fluidly couple to a second fluid supply line;
   a first fluid inlet adapted to fluidly couple to a first fluid return line;
   a second fluid inlet adapted to fluidly couple to a second fluid return line;
   a heat exchanger;
   a pump for circulating fluid from the first and second fluid inlets through the heat exchanger and to the first and second fluid outlets;
   a sensing subsystem adapted to detect if the first fluid outlet becomes disconnected from the first fluid supply line and if the second fluid outlet becomes disconnected from the second fluid supply line; and
   a controller in communication with the pump, the heat exchanger, and the sensing subsystem, the controller adapted to provide a first indication to a user if the first fluid outlet becomes disconnected from the first fluid supply line and to provide a second indication to the user if the second fluid outlet become disconnected from the second fluid supply line.

2. The thermal control unit of claim 1 wherein the first fluid supply line and first fluid return line are coupled to a first patient thermal therapy device, and the second fluid supply line and the second fluid return line are coupled to a second patient thermal therapy device.

3. The thermal control unit of claim 2 wherein the sensing subsystem comprises:
   a first flow meter adapted to measure a first flow rate of the fluid through the first fluid outlet; and a second flow meter adapted to measure a second flow rate of the fluid through the second fluid outlet; and wherein the controller is in electrical communication with the first and second flow meters, and the controller is adapted to provide the first indication if the first flow rate measured by the first flow meter decreases below a threshold and the second indication if the second flow rate measured by the second flow meter decreases below the threshold.

4. The thermal control unit of claim 2 further comprising:
a third fluid outlet adapted to fluidly couple to a third fluid supply line;
a third fluid inlet adapted to fluidly couple to a third fluid return line; and
wherein the sensing subsystem is further adapted to detect if the third fluid outlet becomes disconnected from the third fluid supply line, and wherein the controller is further adapted to provide a third indication to the user if the third fluid outlet becomes disconnected from the third fluid supply line.

5. The thermal control unit of claim 3 further comprising a user interface in electrical communication with the controller, the user interface comprising:
a first graphic that is illuminated a first color when the first flow rate exceeds the threshold and is illuminated a second color when the first flow rate is less than the threshold; and
a second graphic that is illuminated the first color when the second flow rate exceeds the threshold and is illuminated the second color when the second flow rate is less than the threshold.

6. The thermal control unit of claim 5 wherein the user interface is further adapted to allow a user to designate the first fluid outlet as either active or inactive and to designate the second fluid outlet as either active or inactive.

7. The thermal control unit of claim 6 wherein the first graphic is not illuminated when the first fluid outlet is designated as inactive, and the second graphic is not illuminated when the second fluid outlet is designated as inactive.

8. The thermal control unit of claim 7 wherein the first graphic is not visible when the first fluid outlet is designated as inactive and the second graphic is not visible when the second fluid outlet is designated as inactive.

9. The thermal control unit of claim 5 wherein the first color is green and the second color is yellow.

10. The thermal control unit of claim 1 further comprising a first temperature sensor positioned to measure a first temperature of fluid returning to the first fluid inlet, a second temperature sensor positioned to measure a second temperature of fluid returning to the second fluid inlet, and wherein the controller is adapted to display the first and second temperatures on a user interface.

11. The thermal control unit of claim 1 wherein the controller is adapted to operate in a plurality of modes that are selectable by a user, wherein in a first one of the plurality of modes the controller controls a temperature of the fluid pumped to the first and second fluid outlets based on a user-specified fluid target temperature, and wherein in a second one of the plurality of modes the controller controls the temperature of the fluid pumped to the first and second fluid outlets based on a user-specified patient target temperature.

12. The thermal control unit of claim 1 further comprising:
a first patient temperature probe port adapted to receive a first patient temperature probe that measures a first temperature of a patient;
a second patient temperature probe port adapted to receive a second patient temperature probe that measures a second temperature of the patient; and
a user interface adapted to allow a user to choose the first patient temperature probe port or the second patient temperature probe port for use by the controller in controlling a temperature of the fluid pumped to the first and second fluid outlets.

13. The thermal control unit of claim 1 further comprising a removable reservoir adapted to be lifted out of the control unit.

14. The thermal control unit of claim 13 wherein, when the removable reservoir has been lifted out of the control unit, the pump continues to pump the fluid to the first and second outlets and the controller continues to control operation of the heat exchanger.

15. The thermal control unit of claim 13 further comprising a reservoir sensor adapted to detect an absence or presence of the removable reservoir, the reservoir sensor in electrical communication with the controller, wherein the controller is adapted to issue an alert if the reservoir sensor detects the absence of the removable reservoir.

16. The thermal control unit of claim 10 wherein the controller is in electrical communication with the first and second temperature sensors and the controller is adapted to control the heat exchanger based on a mathematical combination of outputs from the first and second temperature sensors.

17. The thermal control unit of claim 16 wherein the mathematical combination is an average of the outputs of the first and second temperature sensors.

18. The thermal control unit of claim 1 further comprising a housing in which the heat exchanger, pump, sensing subsystem, and controller are located; wherein the first and second fluid outlets are positioned at locations such that fluid exits the housing when passing through each of the first and second outlets.

* * * * *